US009265436B2

(12) United States Patent
Min et al.

(10) Patent No.: US 9,265,436 B2
(45) Date of Patent: Feb. 23, 2016

(54) LEADLESS INTRA-CARDIAC MEDICAL DEVICE WITH BUILT-IN TELEMETRY SYSTEM

(75) Inventors: Xiaoyi Min, Thousand Oaks, CA (US); John W. Poore, South Pasadena, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 949 days.

(21) Appl. No.: 13/352,147

(22) Filed: Jan. 17, 2012

(65) Prior Publication Data
US 2013/0116529 A1 May 9, 2013

Related U.S. Application Data

(60) Provisional application No. 61/555,943, filed on Nov. 4, 2011.

(51) Int. Cl.
*A61B 5/0408* (2006.01)
*A61N 1/05* (2006.01)
(Continued)

(52) U.S. Cl.
CPC .............. *A61B 5/042* (2013.01); *A61N 1/3756* (2013.01); *A61N 1/37229* (2013.01); *A61B 5/0006* (2013.01); *A61N 1/368* (2013.01); *A61N 1/3956* (2013.01); *A61N 1/3968* (2013.01)

(58) Field of Classification Search
CPC ....... A61N 1/05; A61N 1/056; A61N 1/0565; A61N 1/057; A61N 1/368; A61N 1/37205; A61N 1/37211; A61N 1/37223; A61N 1/37229; A61N 1/3756; A61N 2001/0585; A61B 5/0408; A61B 5/042; A61B 5/6846; A61B 5/6847; A61B 5/6868; A61B 5/6869; A61B 5/6882
USPC .......... 600/372–375, 377, 509; 607/122, 123, 607/126
See application file for complete search history.

(56) References Cited

U.S. PATENT DOCUMENTS

| 3,835,864 A | 9/1974 | Rasor et al. |
| 3,835,869 A | 9/1974 | Newman et al. |

(Continued)

FOREIGN PATENT DOCUMENTS

| EP | 1844812 A1 | 10/2007 |
| WO | 2005092431 A1 | 10/2005 |
| WO | 2007047681 A2 | 4/2007 |
| WO | 2007047681 A3 | 9/2008 |
| WO | 2009039400 A1 | 3/2009 |
| WO | 2009078751 A1 | 6/2009 |
| WO | 2010088687 A1 | 8/2010 |

OTHER PUBLICATIONS

Asirvatham, Samuel J. MD et al., "Intramyocardial Pacing and Sensing for the Enhancement of Cardiac Stimulation and Sensing Specificity," PACE. 2007;30:748-754.

(Continued)

*Primary Examiner* — Lee S Cohen
*Assistant Examiner* — Erin M Cardinal
(74) *Attorney, Agent, or Firm* — Theresa A. Raymer

(57) ABSTRACT

A leadless intra-cardiac medical device is configured to be implanted entirely within a heart of a patient. The device includes an intra-cardiac extension and a housing. The intra-cardiac extension includes a loop body having at least one loop segment retaining at least one coil group that is configured to one or both of receive and transmit radio frequency (RF) energy, wherein the loop body is configured to extend into a first chamber of the heart. The housing is in electrical communication within the loop body, and includes a transceiver, control logic and an energy source. The housing is configured to be securely attached to an interior wall portion of a second chamber of the heart, wherein the transceiver is configured to communicate with an external device through the RF energy.

13 Claims, 12 Drawing Sheets

(51) Int. Cl.
*A61B 5/042* (2006.01)
*A61N 1/375* (2006.01)
*A61N 1/372* (2006.01)
A61N 1/368 (2006.01)
A61N 1/39 (2006.01)
A61B 5/00 (2006.01)

(56) References Cited

U.S. PATENT DOCUMENTS

| | | | |
|---|---|---|---|
| 3,943,936 | A | 3/1976 | Rasor et al. |
| 4,987,897 | A | 1/1991 | Funke |
| 5,193,540 | A | 3/1993 | Schulman et al. |
| 5,358,514 | A | 10/1994 | Schulman et al. |
| 5,405,367 | A | 4/1995 | Schulman et al. |
| 5,411,535 | A | 5/1995 | Fujii et al. |
| 5,487,758 | A | 1/1996 | Hoegnelid et al. |
| 5,545,201 | A | 8/1996 | Helland et al. |
| 5,679,022 | A | 10/1997 | Cappa et al. |
| 5,766,231 | A * | 6/1998 | Erickson et al. ............... 607/51 |
| 5,814,089 | A | 9/1998 | Stokes et al. |
| 6,141,588 | A | 10/2000 | Cox et al. |
| 6,164,284 | A | 12/2000 | Schulman et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,434,428 | B1 | 8/2002 | Sloman et al. |
| 6,754,536 | B2 | 6/2004 | Swoyer et al. |
| 7,047,076 | B1 | 5/2006 | Li et al. |
| 7,082,336 | B2 | 7/2006 | Ransbury et al. |
| 7,114,502 | B2 | 10/2006 | Schulman et al. |
| 7,363,087 | B2 | 4/2008 | Nghiem et al. |
| 7,383,091 | B1 | 6/2008 | Chitre et al. |
| 7,513,257 | B2 | 4/2009 | Schulman et al. |
| 7,565,195 | B1 | 7/2009 | Kroll et al. |
| 7,634,313 | B1 | 12/2009 | Kroll et al. |
| 7,643,872 | B2 | 1/2010 | Min et al. |
| 7,801,626 | B2 | 9/2010 | Moser |
| 7,860,570 | B2 | 12/2010 | Whitehurst et al. |
| 7,894,915 | B1 | 2/2011 | Chitre et al. |
| 7,899,555 | B2 | 3/2011 | Morgan et al. |
| 7,937,148 | B2 | 5/2011 | Jacobson |
| 7,945,333 | B2 | 5/2011 | Jacobson |
| 8,010,209 | B2 | 8/2011 | Jacobson |
| 8,032,219 | B2 | 10/2011 | Neumann et al. |
| 8,670,842 | B1 * | 3/2014 | Bornzin ............... A61N 1/375 607/125 |
| 2002/0169484 | A1 * | 11/2002 | Mathis ............... A61N 1/3627 607/9 |
| 2004/0015204 | A1 | 1/2004 | Whitehurst et al. |
| 2004/0015205 | A1 | 1/2004 | Whitehurst et al. |
| 2004/0147973 | A1 | 7/2004 | Hauser |
| 2006/0009831 | A1 | 1/2006 | Lau et al. |
| 2006/0135999 | A1 | 6/2006 | Bodner et al. |
| 2006/0241705 | A1 * | 10/2006 | Neumann et al. .............. 607/9 |
| 2007/0055310 | A1 | 3/2007 | Lau |
| 2007/0088396 | A1 | 4/2007 | Jacobson |
| 2007/0088400 | A1 | 4/2007 | Jacobson |
| 2008/0097566 | A1 | 4/2008 | Colliou |
| 2008/0255647 | A1 | 10/2008 | Jensen et al. |
| 2009/0082828 | A1 | 3/2009 | Ostroff |
| 2009/0299433 | A1 | 12/2009 | Dingman et al. |
| 2010/0010381 | A1 | 1/2010 | Skelton et al. |
| 2010/0198288 | A1 | 8/2010 | Ostroff |
| 2011/0071586 | A1 | 3/2011 | Jacobson |
| 2011/0077708 | A1 | 3/2011 | Ostroff |
| 2011/0208260 | A1 | 8/2011 | Jacobson |
| 2011/0218587 | A1 | 9/2011 | Jacobson |
| 2011/0238077 | A1 | 9/2011 | Wenger |
| 2011/0251660 | A1 | 10/2011 | Griswold |
| 2011/0251662 | A1 | 10/2011 | Griswold et al. |
| 2012/0197349 | A1 * | 8/2012 | Griswold ............ A61B 5/0028 607/60 |
| 2013/0085350 | A1 * | 4/2013 | Schugt ............... A61B 5/686 600/302 |
| 2013/0116738 | A1 * | 5/2013 | Samade et al. ............... 607/3 |
| 2013/0116741 | A1 * | 5/2013 | Bornzin ............... A61N 1/3756 607/9 |
| 2013/0123872 | A1 * | 5/2013 | Bornzin et al. ............... 607/17 |
| 2013/0138006 | A1 * | 5/2013 | Bornzin et al. ............... 600/509 |
| 2013/0325081 | A1 * | 12/2013 | Karst et al. ............... 607/25 |
| 2013/0345770 | A1 * | 12/2013 | Dianaty ............... A61N 1/368 607/36 |
| 2014/0100627 | A1 * | 4/2014 | Min ............... 607/32 |
| 2014/0107723 | A1 * | 4/2014 | Hou et al. ............... 607/28 |
| 2014/0172034 | A1 * | 6/2014 | Bornzin et al. ............... 607/17 |

OTHER PUBLICATIONS

Brinker, Jeffrey A., "Endocardial Pacing Leads: The Good, the Bad, and the Ugly," PACE. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," PACE. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: a report of two cases," Heart. 2000;83:351-352.

Henz, Benhur D. MD et al., "Synchronous Ventricular Pacing without Crossing the tricuspid Valve or Entering the Coronary Sinus—Preliminary Results," J Cardiovasc Electrophysiol. (Dec. 2009);20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocarditis on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacmaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," PACE. (Dec. 1990—Pt II);13:1816-1822.

Stellbrink, Christoph et al.,"Technical considerations in implanting left ventricular pacing leads for cardiac resynchronization therapy," European Heart Journal Supplements. 2004;6(Supp D):D43-D46.

Stickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. (Nov. 2004);15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," PACE. 1999;22:823-824.

Restriction Requirement, mailed Jul. 26, 2013—Related U.S. Appl. No. 13/352,101.

NonFinal Office Action, mailed Sep. 9, 2013—Related U.S. Appl. No. 13/352,101.

Notice of Allowance, mailed Feb. 3, 2014—Related U.S. Appl. No. 13/352,101.

* cited by examiner

LEADLESS INTRA-CARDIAC MEDICAL DEVICE WITH BUILT-IN TELEMETRY SYSTEM

CROSS REFERENCE TO RELATED APPLICATIONS

This application relates to and claims priority benefits from U.S. Provisional Application No. 61/555,943, filed Nov. 4, 2011, entitled "Intra-Cardiac Medical Device with Built-In Telemetry System," which is hereby incorporated by reference in its entirety. This application also relates to U.S. patent application Ser. No. 13/352,101, filed Jan. 17, 2012, entitled "Single-Chamber Leadless Intra-Cardiac Medical Device with Dual Chamber Functionality and Shaped Stabilization Intra-Cardiac Extension", now U.S. Pat. No. 8,700,181, which is hereby incorporated by reference in its entirety.

FIELD OF THE INVENTION

Embodiments of the present invention generally relate to implantable medical devices, and more particularly to leadless intra-cardiac medical devices having a built-in telemetry system. As used herein, the term "leadless" generally refers to an absence of electrically-conductive leads that traverse vessels outside of the intra-cardiac space, while "intra-cardiac" means generally, entirely within the heart and associated vessels, such as the SVC, IVC, CS, pulmonary arteries and the like.

BACKGROUND OF THE INVENTION

Current implantable medical devices for cardiac applications, such as pacemakers, include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically excite or pace cardiac tissue and measure or sense myocardial electrical activity.

To sense atrial cardiac signals and to provide right atrial chamber stimulation therapy, the can is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test an implantable device, such as an implantable pacemaker.

To sense the left atrial and left ventricular cardiac signals and to provide left-chamber stimulation therapy, the can is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

To sense right atrial and right ventricular cardiac signals and to provide right-chamber stimulation therapy, the can is coupled to an implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Although a portion of the leads are located within the heart, a substantial portion of the leads, as well as the can itself are outside of the patient's heart. Consequently, bacteria and the like may be introduced into the patient's heart through the leads, as well as the can, thereby increasing the risk of infection within the heart. Additionally, because the can is outside of the heart, the patient may be susceptible to Twiddler's syndrome, which is a condition caused by the shape and weight of the can itself. Twiddler's syndrome is typically characterized by a subconscious, inadvertent, or deliberate rotation of the can within the subcutaneous pocket formed in the patient. In one example, a lead may retract and begin to wrap around the can. Also, leads may dislodge from the endocardium and cause the device to malfunction. Further, in another typical symptom of Twiddler's syndrome, the device may stimulate the diaphragm, vagus, or phrenic nerve, pectoral muscles, or brachial plexus. Overall, Twiddler's syndrome may result in sudden cardiac arrest due to conduction disturbances related to the device.

In addition to the foregoing complications, implanted leads may experience certain further complications, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM) are typically characterized by the following features: they are devoid of leads that pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

It can be appreciated, however, that a leadless pacing system needs to be compact enough to fit within the heart. At the same time, the pacing system requires a power source to operate. Accordingly, the pacer module includes a battery contained therein. Typically, the pacer module has a housing having a battery that may take up as much as 75% of the internal volume of the housing. Therefore, the pacer module itself may be bulky and occupy a relatively large volume within the heart chamber, which may adversely impact proper heart function.

Moreover, many pacing systems include telemetric subsystems that communicate with a remote programmer or patient care system. Telemetric subsystems include an antenna that communicates with the remote patient care system through radio frequency (RF) signals. Conventional antenna are relatively large, too large to fit into the housing of a leadless pacemaker.

SUMMARY OF THE INVENTION

Certain embodiments provide a leadless intra-cardiac medical device (LIMD) configured to be implanted entirely within a heart of a patient. The device includes an intra-cardiac (IC) extension and a housing. The intra-cardiac extension may include a loop body having at least one loop segment retaining at least one coil group that is configured to receive and/or transmit radio frequency (RF) energy. The loop body may be configured to extend into a first chamber of the heart.

The housing is in electrical communication within the loop body and is configured to be securely attached to an interior wall portion of a second chamber of the heart. The housing includes a transceiver that is configured to communicate with an external device through the RF energy.

The housing further includes an energy source that may be configured to be recharged through current induced within the at least one coil group. The current may be induced by a magnetic field caused by the RF energy. The loop segment may include at least one electrode secured thereto. The loop segment may be configured to contact a portion of an internal wall of the heart. The housing may be configured to provide one or both of sensing or stimulus through the at least one electrode.

The loop segment may include a plurality of interconnected loop segments. Each of the plurality of interconnected loop segments may be commonly aligned and oriented with respect to one another and a reference plane. Alternatively, the plurality of interconnected loop segments may include a first group of loop segments and a second group of loop segments. The first group of loop segments may be oriented with respect to first and second orthogonal axes and the second group of loop segments may be oriented with respect to first and third orthogonal axes. A first of the plurality of interconnected loop segments may be aligned in a first orientation and a second of the plurality of interconnected loop segments may be aligned in a second orientation. The first orientation differs from the second orientation so that the first and second of the plurality of interconnected loop segments are out of plane with one another.

The loop segments may be formed with a perimeter that flares in a direction generally toward and away from a lateral axis with respect to a longitudinal axis of the loop body. The loop segments may include a perimeter shaped as a disc, oval, circle, tube, rectangle, or triangle.

The IMD system may also include a protective tube between the loop body and the housing. The loop segments may be proximally or distally located from the housing.

Certain embodiments provide a method of operating a leadless intra-cardiac medical device (LIMD) within a heart of a patient. The device may include a loop body having at least one loop segment retaining at least one coil group within a first internal portion of the heart, and a housing connected to the loop body and secured within a second internal portion of the heart. The method may include emitting radio frequency (RF) energy from an external device to the IMD, generating an induced current in the loop body through the RF energy, passing the induced current from the loop body within the first internal portion of the heart to the housing secured within the second internal portion of the heart, and communicating between the IMD and the external device through the generating and passing.

The method may also include recharging a rechargeable energy source of the LIMD through the induced current.

The method may also include contacting an internal wall of the first internal portion of the heart with at least one electrode on a portion of the loop body. The at least one housing may be configured to provide one or both of sensing or stimulus through the at least one electrode.

The method may also include calibrating the LIMD after implantation into the heart of the patient. The calibrating may include adjusting drive frequencies of the at least one loop segment. The method may also include tuning the loop segments through the adjusting.

DETAILED DESCRIPTION

Figure 1:
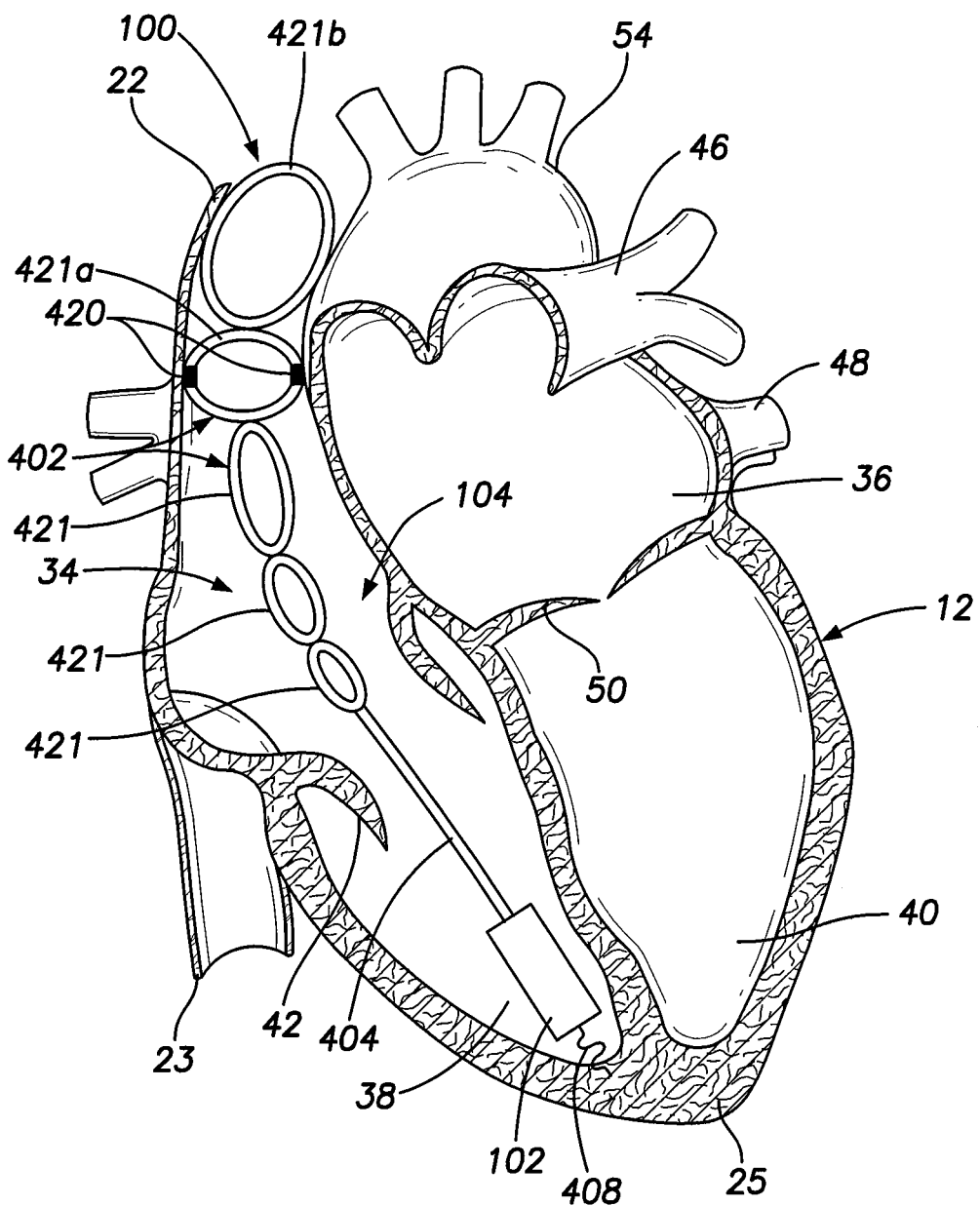
FIG. 1 illustrates a leadless intra-cardiac medical device (LIMD) implanted within a heart of a patient that includes housing and an intra-cardiac extension.

FIG. 1 illustrates a leadless intra-cardiac medical device (LIMD) 100 implanted within a heart 12 of a patient, according to an embodiment. The heart 12 is generally enclosed in a pericardium, which protects the heart 12, anchors its surrounding structures, and prevents overfilling of the heart 12 with blood. The heart 12 has four chambers, a right atrium 34, a left atrium 36, a right ventricle 38, and a left ventricle 40. In general, the atria 34 and 36 are the receiving chambers, while the ventricles 38 and 40 are the discharging chambers. Deoxygenated blood enters the heart 12 through the superior vena cava 22 or inferior vena cava 23, for example, and passes into the right atrium 34. The blood is then pumped through the tricuspid valve 42 into the right ventricle 38 before being pumped out through a pulmonary valve (not shown) into a pulmonary artery 46. The blood is then oxygenated in the lungs and returns to the heart 12 through a pulmonary vein 48 into the left atrium 36, where it is then pumped through the mitral valve 50 and into the left ventricle 40. The oxygenated blood then travels from the left ventricle 40 through the aortic valve (now shown) and into the aorta 54, through which the oxygenated blood is then circulated throughout the body.

The LIMD 100 is implanted entirely within the heart 12. The LIMD 100 includes a housing 102 configured to be secured to a tissue wall, for example the wall defining the right ventricle 38 proximate an apex 25 of the heart 12. The housing 102 is operatively connected to an intra-cardiac extension 104 that includes a loop body 402 having multiple loop segments 421, with the loop segments 421a and 421b being passively secured within the superior vena cava 22, as explained below. Electrodes 420 are included in the loop segment 421a on either side and contact interior wall portions of the superior vena cava 22. In one embodiment, the intra-cardiac extension 104 is fixedly connected to, and hermitically sealed together with, the electronics housing 102. In this case, the intra-cardiac extension 104 cannot be disconnected from the electronics housing 102 and the LIMD is thus, in essence a single unitary structure. In other embodiments, the intra-cardiac extension 104 may be connected to the electronics housing 102 through a pin/port connection arrangement, in which case the intra-cardiac extension 104 may be disconnected from the electronics housing 102. This configuration may allow for customization in the form of different sized intra-cardiac extensions for different sized cardiac anatomies.

Figure 2:
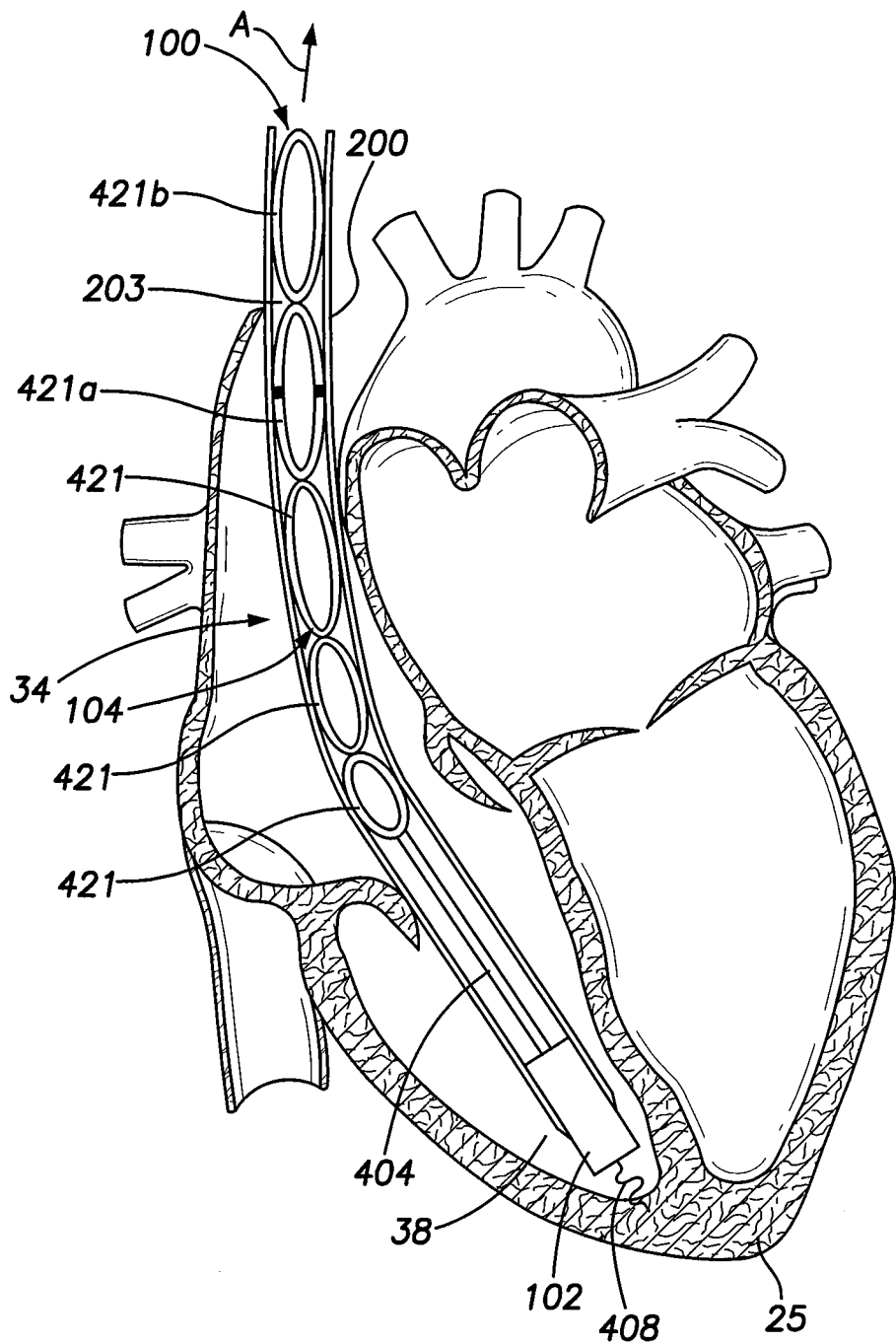
FIG. 2 illustrates an introducer assembly introducing an LIMD into a heart of a patient.

FIG. 2 illustrates an introducer assembly 200 introducing the LIMD 100 into the heart 12, according to an embodiment. The introducer assembly 200 includes a flexible tube, such as a catheter, having an internal longitudinal passage 203 into which the LIMD 100, including the loop body 402 and the housing 102, are retained. The introducer assembly 200 is maneuvered by a physician at a proximal end (not shown) into the heart 12 such that the housing 102 is positioned in the right ventricle 38 proximate the apex 25. The housing 102 is then anchored in place through a securing helix 408.

The introducer assembly 200 is then pulled back in the direction of arrow A, leaving the housing 102 secured to the heart 12 within the right ventricle 38. The introducer assembly 200 disengages from the LIMD 100 as it is pulled away in the direction of arrow A.

Figure 3:
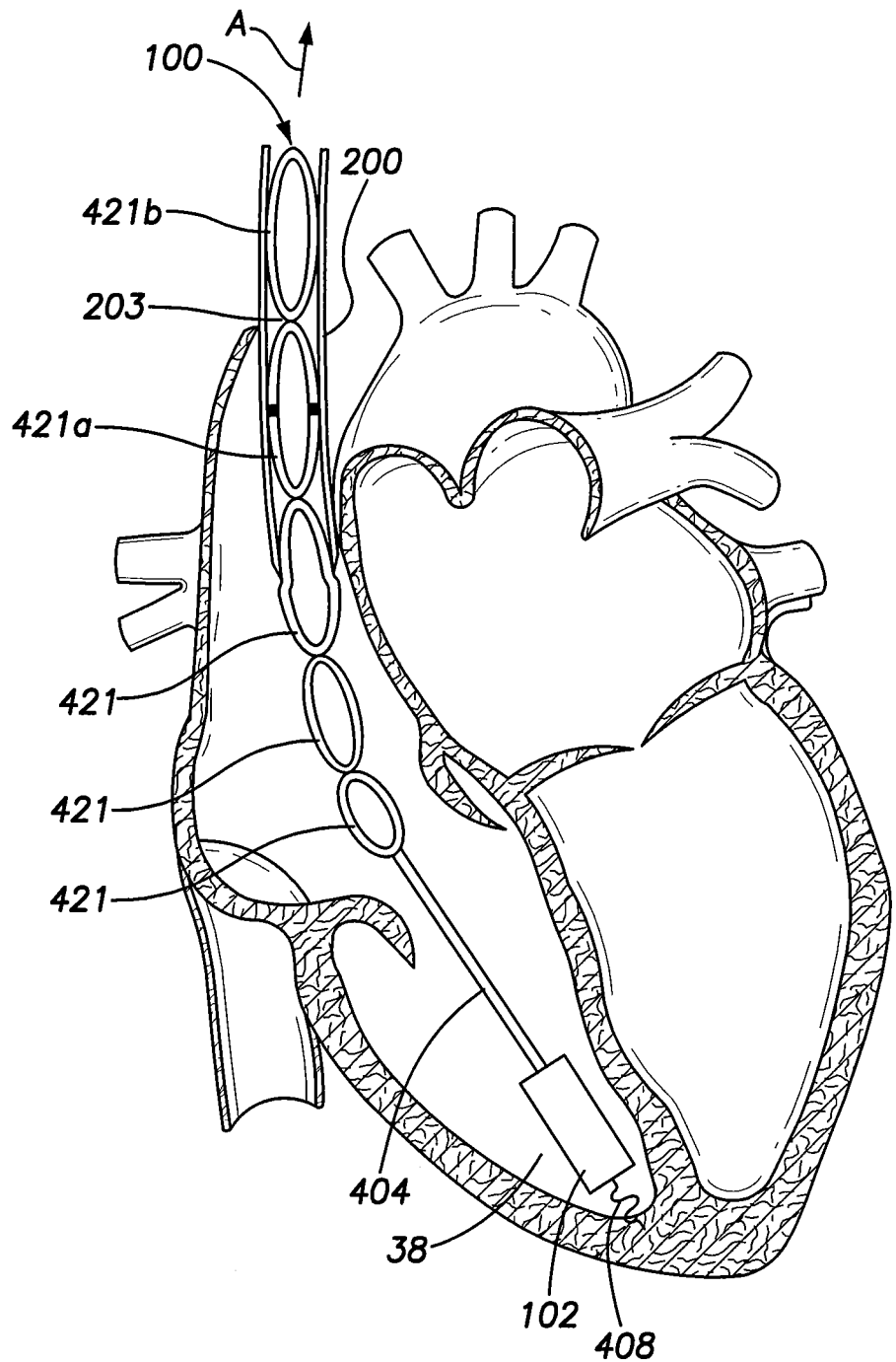
FIG. 3 illustrates an introducer assembly disengaging from an LIMD within a heart of a patient.

FIG. 3 illustrates the introducer assembly 200 disengaging from the LIMD 100 within the heart 12, according to an embodiment. As the introducer assembly 200 is pulled back in the direction of arrow A, the anchored housing 102 ensures that the LIMD 100 does not retreat along with the introducer assembly 200. As the introducer assembly 200 slides back in the direction of arrow A, the flexible loop segments 421, which were previously compressed within the introducer assembly 200, are ejected and expand outwardly. Once the introducer assembly 200 fully disengages from the LIMD 100, the LIMD 100 is implanted entirely within the heart 12, as shown in FIG. 1.

Figure 4A:
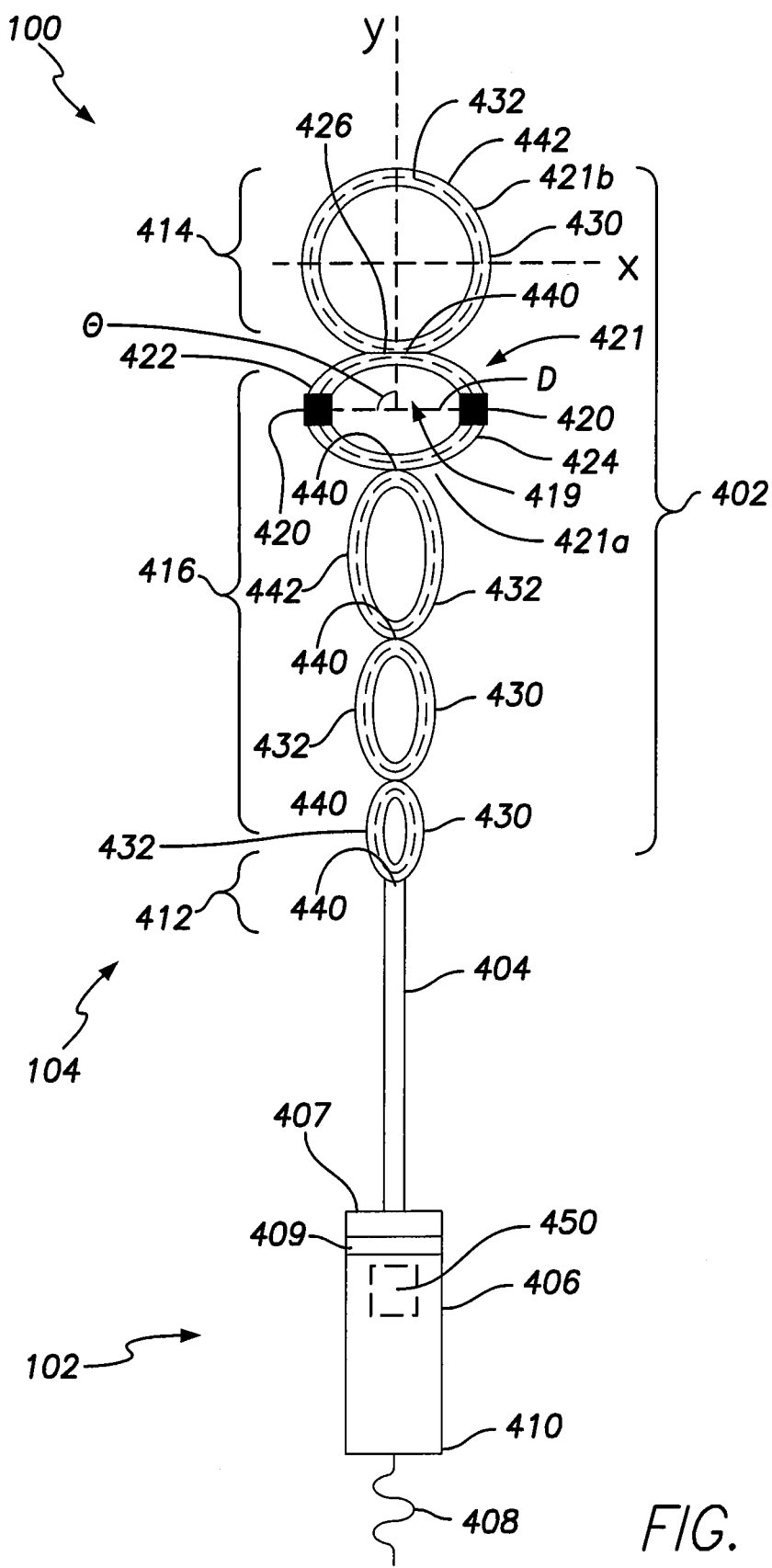
FIG. 4A illustrates an LIMD.

FIG. 4A illustrates the LIMD 100 outside of a heart. The LIMD 100 includes a housing 102 and an intra-cardiac extension 104 that extends from an end of the module. The intra-cardiac extension 104 has a loop body 402 connected to a protective tube 404, such as an insulated sheath, sleeve, or the like. The LIMD 100 may be one of various types of implantable devices, such as, for example, an implantable pacemaker, a cardiac resynchronization therapy (CRT) device, an implantable cardioverter-defibrillator ("ICD"), neurostimulator, or the like. The IMD 100 may be configured for DDDR pacing (atrial and ventricular pacing, atrial and ventricular sensing, dual response and rate-adaptive, used for dual chamber pacemakers). In one embodiment, the housing 102 includes a cylindrical body 406 having a base 410 and a top end 407. A securing helix 408 extends from the base 410 of the body 406 and is configured to securely anchor the body 406, and therefore the housing 102, to tissue within a chamber of a heart. Instead of a securing helix 408, a barb, hook, or the like may extend from the body 406. The tube 404 includes insulated conductors that are covered with insulation to mechanically and electrically connect the housing 102 to the loop body 402. The tube 404 and loop body 402 may be formed as a single integral structure. Furthermore, the tube 404 and the loop body 402 may be formed to have substantially uniform stiffness along the entire length. Alternatively, portions of the intra-cardiac extension 104 formed by the loop body 402 and tube 404 may have varying stiffness properties and/or shape memory properties. For example, the tube 404 portion may have no shape memory properties and be less stiff then the loop body 402. The loop body 402 may have different properties along its length. For example, the most distal loop segments 421a, 421b may have shape memory properties and greater stiffness than the more proximal loop segments, which may or may not have shape memory properties.

The housing 102 may include one or more pairs of electrodes for providing pacing and sensing capabilities. For example, in one configuration, a portion of the helix 408 may be electrically conductive and function as an electrode. A second electrode 409 may be in the form of a ring around the outer surface of the body 406. The electrodes 408, 409 may be configured to deliver lower energy or high energy stimulus, such as pacing pulses, cardioverter pulse trains, defibrillation shocks and the like. The electrodes 408, 409 may also be used to sense electrical activity, such as physiologic and pathologic behavior and events.

The loop body 402 of the intra-cardiac extension 104 includes a proximal portion 412, a distal end portion 414, and an intermediate portion 416 extending between the proximal portion 412 and the distal end portion 414. The loop body 402 includes a series of loop segments 421 that may have concentric circular openings 419 through center regions of each loop segment 421 (for example, similar to a donut). One or more sensing and/or stimulus electrodes 420 may be provided on one or more of the loop segments 421. The electrodes 420 are spaced apart from one another by an inter-electrode spacing (for example, the diameter of the loop segment 421). The electrodes 420 may be wrapped around, or otherwise secured to, a peripheral portion of a loop segment 421. As shown in FIG. 4A, two electrodes 420 are secured around circumferential portions of the loop segment 421a at diametrically opposite sides 422 and 424. The loop segments 421 are joined to one another at connection links or joints 426. As shown, the electrodes 420 are distally located from one another on the loop segment 421a and may be positioned generally at a radial angle η that is 90° from a connection link or joint 426 with loop segment 421b, for example. The opposed electrodes 420 are configured to contact tissue portions within a heart, as explained below. The number of electrodes 420 may vary depending on a particular application. For example, additional electrodes may be secured to the loop segment 421b, or any of the other loop segments 421. Additionally, while the electrodes 420 are shown at opposite sides 422 and 424 of the loop segment 421a, the electrodes 420 may be positioned at various other locations on the loop segments 421, and even at different locations from connection joints 426. Also, more or less electrodes 420 than those shown on the loop segment 421a may be used. For example, the loop segment 421a may include only one electrode 420.

The electrodes 420 may be configured to deliver lower energy or high energy stimulus, such as pacing pulses, cardioverter pulse trains, defibrillation shocks and the like. The electrodes 420 may also be used to sense electrical activity, such as physiologic and pathologic behavior and events.

Figure 4B:
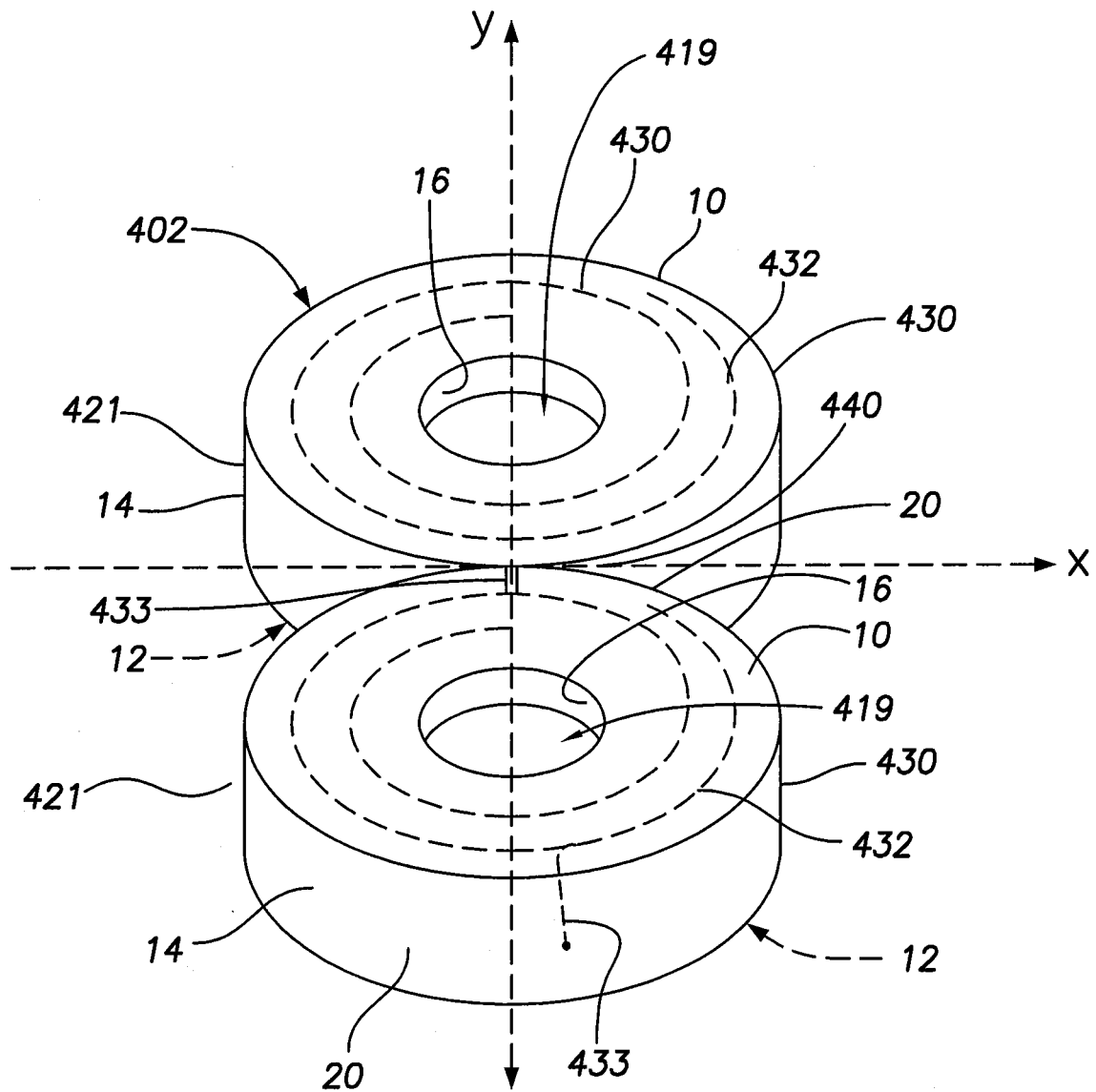
FIG. 4B illustrates an isometric view of adjacent loop segments of a loop body of an intra-cardiac extension.

Each electrode 420 is electrically isolated from the other electrodes 420 and from a telemetry conductor 430 contained within the loop segments 421. Separate terminals and wires (not shown) join the electrodes 420 and the telemetry conductor 430 to the associated electronics in the IMD 100. The telemetry conductor 430 is provided within the loop segments 421 of the loop body 402. With reference to FIG. 4B, the telemetry conductor 430 includes windings that are wound into a series of coil groups 432 to form inductive loops. Each coil group 432 may include windings of the insulated conductive wire between 1 and 1000 turns, for example. The coil groups 432 operate to receive and/or transmit radio frequency (RF) energy. The windings in the coil groups 432 may be formed in a variety of patterns from generally uniformly shaped circles, ovals and the like. However, the windings or inductive loops of the coil groups 432 are wound in a uniform shape and each coil group 432, that is connected in series, is wound in a common direction about a corresponding axis. For example, if one winding is wound in a clock-wise direction about an axis of the associated coil group 432, then all of the windings joined in series therewith may be wound in the same clock-wise direction about the same axis or associated axes of other coil groups 432. Alternatively, if one winding is wound in a counter-clock-wise direction about an axis of the associated coil group 432, then all of the windings joined in series therewith may be wound in the same counter-clock-wise direction about the same axis or associated axes of other coil groups. As shown, the telemetry conductor 430 is not shown in any specific winding pattern. But it is understood that the telemetry conductor 430 may be wound in any desired manner to receive and transmit RF energy that represents communications signals to and from an external programming device.

The telemetry conductor 430 may also be wound with a number of turns and wire gauge sufficient to receive RF energy that represents power that is then used to charge a battery of the housing 102 joined to the proximal portion 412 of the loop body 402. A telemetry circuit 450 included in the housing 102 receives signals (e.g., power or data) induced into the telemetry conductor 430 by RF energy passing about the coil groups 432. The coil groups 432 include at least one partial winding of the telemetry conductor 430. Optionally, at least one of the coil groups 432 may include multiple windings that are at least partially spatially overlapped with one another. The coil groups 432 are distributed along the loop body 402 and positioned to be centered along a longitudinal axis. The telemetry conductor 430 is surrounded by a thin film insulation (for example, Silicone, OPTIM, polyurethane) to electrically separate adjacent windings such that the inductive loops of each coil group 432 are insulated from one another (for example, ETFE).

The coil groups 432 may be formed of a single conductive wire, for example, that connects to the telemetry circuit 450 (discussed below). For example one end of the wire may connect to the telemetry circuit and extend through the tube 404 and extend from the coil groups 432, with the other end connecting back to the telemetry circuit 450. As such, a single conductive wire may be contained within all of the loop segments. The single conductive wire forms the coil groups 432 within each loop segment 421, and extends to another loop segment through a straight line that passes through the connection joint 426. Optionally, each coil group 432 may include a separate and distinct wire coil having first and second ends that connect to the telemetry circuit 450.

In accordance with at least one embodiment, one or more of the loop segments 421 of the loop body 402 are configured to have shape memory properties such that they may be squeezable or compressible into a smaller profile that allows them to be loaded into the introducer assembly 200 (shown in FIGS. 2 and 3), such as a cardiac catheter. For example, the use of the metal braid or mesh core surrounded by silicon, ETFE, OPTIM and the like may be sufficient to afford the desired amount of shape memory. In the absence of a compressing force, e.g., upon release from the introducer assembly, the loop segments assume their normally expanded shape having a larger profile. A guiding wire may be attached to the loop body 402 during implantation into a heart. After the loop body 402 is in place, the introducer assembly 200 is extruded to the last loop segment 421 with a guiding wire holding the last loop segment 421. Pacing/sensing tests may be performed before the system is completely released. If another location attempt is needed, the guiding wire may retract the system.

Optionally, a thermo-responsive shape memory polyurethane (SMPU) may be embedded below and encased within a biocompatible shell (e.g., EFTE). The SMPU represents a smart material that can respond to external heat by changing its macroscopic shape from a temporary configuration to a memorized permanent one. The temporary elongated shape can be maintained while in the sheath which may maintain a certain temperature (the transition temperature). The sheath may maintain the loop segments 432 at this temperature until discharged, after which the material of the loop segments 432 may change temperature. Thereafter, the material in the loop segments 432 will recover its memorized permanent shape.

The loop segments 421 are located immediately adjacent one another and may be formed integral with one another. The loop segments 421 may be joined with one another by linking regions 440, such as the connection joints 426. For example, the intermediate portion 416 may be joined to the distal end portion 414 through a linking region 440. The loop segments 421, linking regions 440, and distal end portion 414 may be formed integral with one another from a biocompatible electrically insulating material, such as silicon, polyurethane, or other materials such as copolymers (for example, the Optim® insulation offered by St. Jude Medical, Inc.).

The loop segments 421 have a perimeter 442 that may be flared (for example, diverges and then re-merges) in a direction generally toward and away from the lateral axis x with respect to the longitudinal axis y of the loop body 402. The loop segments 421 may have different contoured shapes, as shown in FIG. 4A. By way of example, the loop segments 421 may have a perimeter, when viewed from the top down, that is disc-shaped, oval, circular, tubular, rectangular, triangular, and the like.

The loop segments 421 have opposed top and bottom sides that are aligned generally in parallel planes that extend in a generally common direction as the longitudinal axis y. The loop segments 421 are aligned along a common path. It is recognized that, while FIG. 4A illustrates the loop segments 421 aligned in a straight manner, this is for illustration purposes. When implanted, the loop segments 421 will curve and wrap to follow the contour of an interior of the heart in a manner determined by the implanting physician.

FIG. 4B illustrates an isometric view of adjacent loop segments 421 of the loop body 402 of the intra-cardiac extension 421. Each loop segment 421 includes opposed planar sides 10 and 12 that integrally connect to a peripheral edge 14 and an internal edge 16 that defines the opening 419.

The adjacent loop segments 421 are joined at opposite sides along a longitudinal axis x. Each loop segment 421 includes a coil group 432 encased therein. The telemetry conductor 430 may form the coil groups 432. Each coil group 432 may include windings arranged in a common plane parallel to the opposed planar sides 10 and 12 as well as the peripheral and internal edges 14 and 16. The coil groups 432 may be formed of a single conductive wire that forms the telemetry conductor 430, with connective wire portions 433 within the linking regions 440 that interconnect the coil groups 432.

Referring again to FIG. 4A, device electronics (not shown) are provided within the housing 102. The electronics and their related functions may vary depending upon a particular implementation. By way of example, the electronics may include all of the control logic needed to implement an implantable medical device, such as but not limited to an implantable pacemaker, cardioverter, defibrillator, neurostimulator and the like. The electronics includes one or more rechargeable energy sources such as a rechargeable battery. The electronics may also include a charge storage device depending upon the functionality to be performed. For example, if the IMD 100 delivers stimulus pulses, the charge storage device may include one or more capacitors that are sufficient in capacity to deliver the desired stimulus. Alternatively, the electronics may have a more limited subset of components configured to implement only a portion of the functionality available in an implantable medical device.

Figure 5:
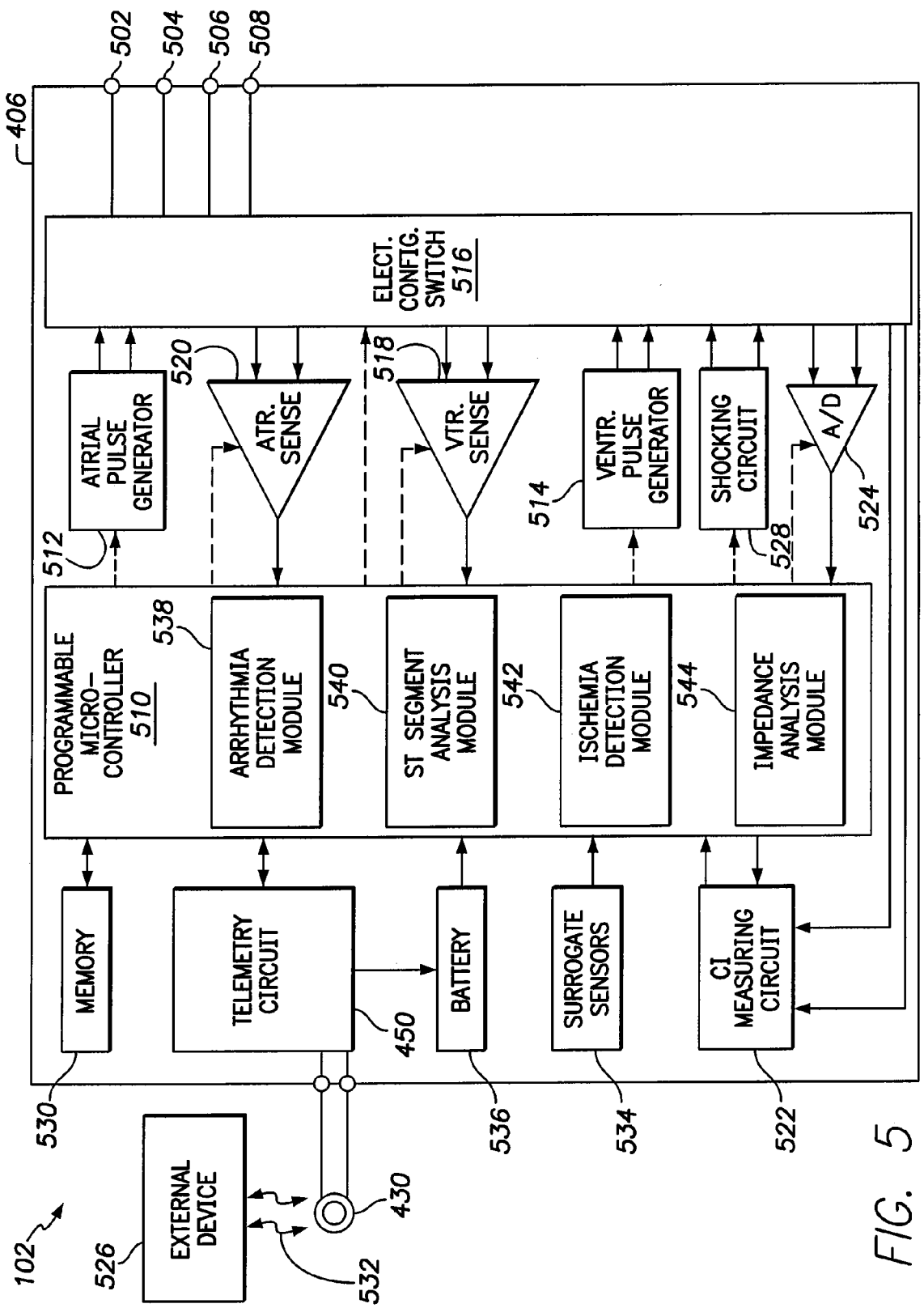
FIG. 5 illustrate a block diagram of electronics associated with the housing of an LIMD.

FIG. 5 illustrates a block diagram of a housing 102 portion of an LIMD 100, which may be capable of treating one or both of fast and slow arrhythmias with stimulation therapy, including cardioversion, defibrillation, and pacing stimulation, according to an embodiment. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

By way of example only, the housing 102 may form part of a "nano" pacemaker that may be packaged in a very compact and small manner having a form factor substantially similar to the form factor of the loop body 402. The body 406 of the device housing 102 may have a cross-section that is no larger than the cross-section of the loop body 402. Alternatively, the housing may have a disc shape when viewed from the top down and have a small thickness or height, where the disc shape and the thickness/height are substantially the same as the disc shape and thickness of the loop body.

The body 406 of the housing 102 is often referred to as the "can", "case" or "case electrode" and may be programmably selected to act as the return electrode for some or all sensing modes. The body 406 may further be used as a return electrode alone or in combination with one or more of the other electrodes. The electronics within the housing 102 include a plurality of terminals 502, 504, 506, 508. To achieve sensing, pacing and shocking in desired chambers of the heart, the terminals are selectively connected to corresponding combinations of electrodes, including electrodes 408, 409 on the housing 102 and electrodes 420 on the intra-cardiac extension 104.

The housing 102 includes a programmable microcontroller 510 that controls the various modes of sensing and stimulation therapy. The microcontroller 510 includes a microprocessor, or equivalent control circuitry, designed specifically for controlling the delivery of stimulation therapy and may further include RAM or ROM memory, logic and timing circuitry, state machine circuitry, and I/O circuitry. The microcontroller 510 includes the ability to process or monitor input signals (data) as controlled by a program code stored in memory. The details of the design and operation of the microcontroller 510 are not critical. Rather, any suitable microcontroller 510 may be used. The microcontroller 510 may analyze sensed signals and determine when an arrhythmia (e.g., fibrillation) is occurring. The microcontroller 510 may detect arrhythmias, such as ventricular tachycardia (VT), bradycardia and ventricular fibrillation (VF). The microcontroller 510 may perform morphology detection to analyze the morphology of the cardiac signal, including detecting R wave peaks and/or detecting T wave features of interest, such as onset, peak, etc.

The housing 102 includes a rechargeable or non-rechargeable battery 536 and one or more energy storage units 512, 514, 528, such as a plurality of capacitors. The energy storage units may vary depending upon the functionality desired to be supplied by the housing 102. For example, when the housing 102 affords all of the functionality of a defibrillator, the storage unit represents a shocking circuit 528 having high voltage capacitors capable of storing large amounts of energy needed to deliver defibrillation shocks. When the housing 102 electronics functions as a pacemaker, the storage unit may represent an atrial pulse generator 512 and/or a ventricular pulse generator 514 having capacitors capable of storing the amount of energy needed to delivery low voltage pacing pulses.

Control logic is provided on an integrated circuit (IC). The control logic includes various electronic components based on the desired functionality of the housing 102. By way of example, the control logic includes the processor 510, a switching bridge 516, and analog-to-digital (A/D) converters 524. The switching bridge 516 interfaces with multiple input terminals 502, 504, 506, 508 that are configured to be coupled to terminals connected to the atrial electrodes 420 and the ventricular electrodes 408, 409 through wires within the intra-cardiac extension 104. Optionally, more inputs may be includes based on the number of electrodes and telemetry coils.

The housing 102 includes the telemetry circuit 450 that is configured to receive signals that are detected by the telemetry conductor 430, as well as transmit signals to the telemetry conductor 430 that are then wirelessly transmitted as RF energy to an external device 526. The telemetry circuit 450 includes a transceiver that performs modulation upon outgoing data signals and performs demodulation upon incoming data signals. For example, the telemetry conductor 430 may receive, in the RF energy, data signals such as commands, parameters, thresholds and the like. As one optional exemplary implementation for incoming data, the telemetry circuit 450 may detect analog data signals sensed by the coil groups 432, convert the analog data signals into digital data packets and convey the data packets to the processor 510. As one optional exemplary implementation for outgoing data, the telemetry circuit 450 receives data packets from the processor 510, converts the data packets to analog data signals and transmits the analog data signals over the coil groups 432. Optionally, for outgoing data transmissions, the telemetry circuit 450 may packetize data segments in accordance with a predetermined wireless transmission protocol, such as by dividing an outgoing data stream into segments, and packetize each data segment with header and footer information. Similarly, incoming data transmissions may be formatted in accordance with a predetermined transmissions protocol. The telemetry circuit 450 may temporally buffer incoming data transmissions, parse the stored inbound data stream for header and/or footer information, and extract the data content from the inbound data stream. The telemetry circuit 450 may then convey data content to the processor 510 with or without reformatting and/or repackaging the data content.

With respect to the rechargeable battery 536, the telemetry conductor 430 may receive, through RF energy, a power signal that is used to recharge the battery 536. A power conversion unit (not shown) converts RF energy received on telemetry conductor 430 into a power supply signal that can recharge the battery 536 (for example, to a desired voltage range and/or current level). As explained below, the RF energy generates a magnetic field, which, in turn, induces a current within the loop segments that is used to recharge the battery 536. Optionally, the telemetry conductor 430 may receive power in the RF signal that is routed directly to an energy storage unit 512, 514, 528 to directly charge capacitors before the capacitors deliver a low or high energy stimulus (for example, pace or defibrillation.)

The atrial pulse generator 512 and a ventricular pulse generator 514 generate pacing and ATP stimulation pulses for delivery by desired electrodes. The electrode configuration switch 516 (also referred to as switch bank) controls which terminals 502, 504, 506, 508 receive electrical signals, shocks or pacing pulses. The pulse generators 512, 514 are controlled by the microcontroller 510 via appropriate control signals respectively, to trigger or inhibit stimulation pulses. The microcontroller 510 controls the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

A ventricular sensing circuit 518 may amplify, filter, digitize and/or otherwise process cardiac signals sensed using the electrodes. The circuit 518 may provide separate, combined or difference signals to the microcontroller 510 representative of the sensed signals from the RV electrodes 408, 409. An atrial sensing circuit 520 is connected through the switch 516 to RA electrodes 420 to sense RA cardiac activity. The switch 516 also connects various combinations of the electrodes to an impedance measurement circuit 522.

The impedance measuring circuit 522 collects impedance measurements between corresponding combinations of electrodes. For example, the impedance measuring circuit 522 may collect measured impedance for each or a subset of the sensing vectors. The impedance measurements are taken along one or more vectors through the heart over a period of time. The impedance measurements are supplied to the controller 510.

The switch 516 determines the "sensing polarity" of the cardiac signal by selectively closing the appropriate switches. The outputs of the atrial and ventricular sensing circuits 518, 520 are connected to the microcontroller 510 which, in turn, is able to trigger or inhibit the atrial and ventricular pulse generators 512, 514, respectively. The sensing circuits 518, 520, in turn, receive control signals over signal lines from the microcontroller 510 for purposes of controlling the gain, threshold, the polarization charge removal circuitry (not shown), and the timing of any blocking circuitry (not shown) coupled to the inputs of the sensing circuits 518, 520.

Cardiac signals are also applied to the inputs of an analog-to-digital (ND) data acquisition system 524. The data acquisition system 524 is configured to acquire intracardiac electrogram signals, convert the raw analog data into a digital signal, and store the digital signals for later processing and/or telemetric transmission to an external device 526. The data acquisition system 524 samples cardiac signals across any pair of desired electrodes. The microcontroller 510 further controls the shocking circuit 528 by way of a control signal. The shocking circuit 528 generates stimulating pulses of low (up to 0.5 Joules), moderate (0.5-10 Joules), or high energy (11 to 40 Joules), as controlled by the microcontroller 510. Stimulating pulses are applied to the patient's heart through at least two shocking electrodes.

The microcontroller 510 is further coupled to a memory 530 by a suitable data/address bus. The memory 530 stores programmable operating, impedance measurements, impedance derivation and therapy-related parameters used by the microcontroller 510. The operating and therapy-related parameters define, for example, surrogate signals, contractility estimates, models, length force curves, correction factors, trend values, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 530 through the telemetry circuit 450 in telemetric communication with the external device 526, such as a programmer, trans-telephonic transceiver, or a diagnostic system analyzer. The telemetry circuit 450 is activated by the microcontroller 510. The telemetry circuit 450 advantageously allows intracardiac electrograms, cardiogenic impedance (CI) measurements, surrogate signals, contractility estimates, correction factors, models, trend values and status information relating to the operation of the LIMD 100 to be sent to and from the external device 526 through an established communication link 532.

The housing 102 may include one or more surrogate sensors 534. The surrogate sensor(s) 534 produces surrogate signals representative of estimates for at least one of cardiac volume and pressure of the heart when the impedance measurements were taken. For example, the surrogate sensor 534 may sense estimates of end diastolic volume, blood pressure, heart rate, stroke volume, patient activity, respiration rate and the like. Optionally, the surrogate sensor 534 may produce surrogate signals by identifying features of interest form the impedance measurements. For example, the sensor 534 may collect and filter impedance signals along one or more impedance sensing vectors. The sensor 534 may include a low-pass, band pass and/or high pass filter to filter the impedance measurements and produce non-contractility information.

The sensors 534 may include one or more of an accelerometer, a pressure sensor, a heart sound sensor, a pulse oximetry sensor, a flow sensor and the like. While a sensor 534 is shown within the housing, optionally, one or more sensors may be located outside the housing and coupled thereto through a connector. The sensor 534 may detect a level of or changes in cardiac output, a level of changes in the physiological condition of the heart, or a level of or changes in activity (e.g., detecting sleep and wake states). The battery 536, such as the rechargeable battery discussed above, provides operating power to all of the circuits shown.

The controller 510 includes, among other things, various modules to perform select types of analysis. For example, an arrhythmia detection module 538 may analyze sensed signals and identifies various types of arrhythmias. An ST segment analysis module 540 may analyze various characteristics of ST segments over multiple cardiac cycles to identify changes or patterns that are indicative of certain conditions of interest. An ischemia detection module 542 may analyze sensed signals to identify different types of ischemia. An impedance analysis module 544 may analyze impedance measurements and, based thereon, derive estimates of cardiac output and the like.

When the LIMD 100 is located deep within the heart, as compared with subcutaneous implants, the signals transmitted to/from the coil groups 432 may be weaker. Optionally, more or fewer coil windings may be included within each coil group 432 depending upon whether the intra-cardiac extension 104 is intended to be implanted shallower or deeper. Embodiments described herein may utilize waved multi-loop coil groups 432. Each coil group 432 represents an inductor. By joining the coil groups 432 electrically in series, a series of inductors are formed to achieve coupling and signal linkage through telemetry with desired implanted or external components.

By way of example, the insulated wires of the electrodes 420 and the telemetry conductor 430 may be made of biocompatible metals (DFT or Copper, or the like). The coating of the wires may be ETFE and the wires may be embedded inside Silicone or another material.

Figure 6:
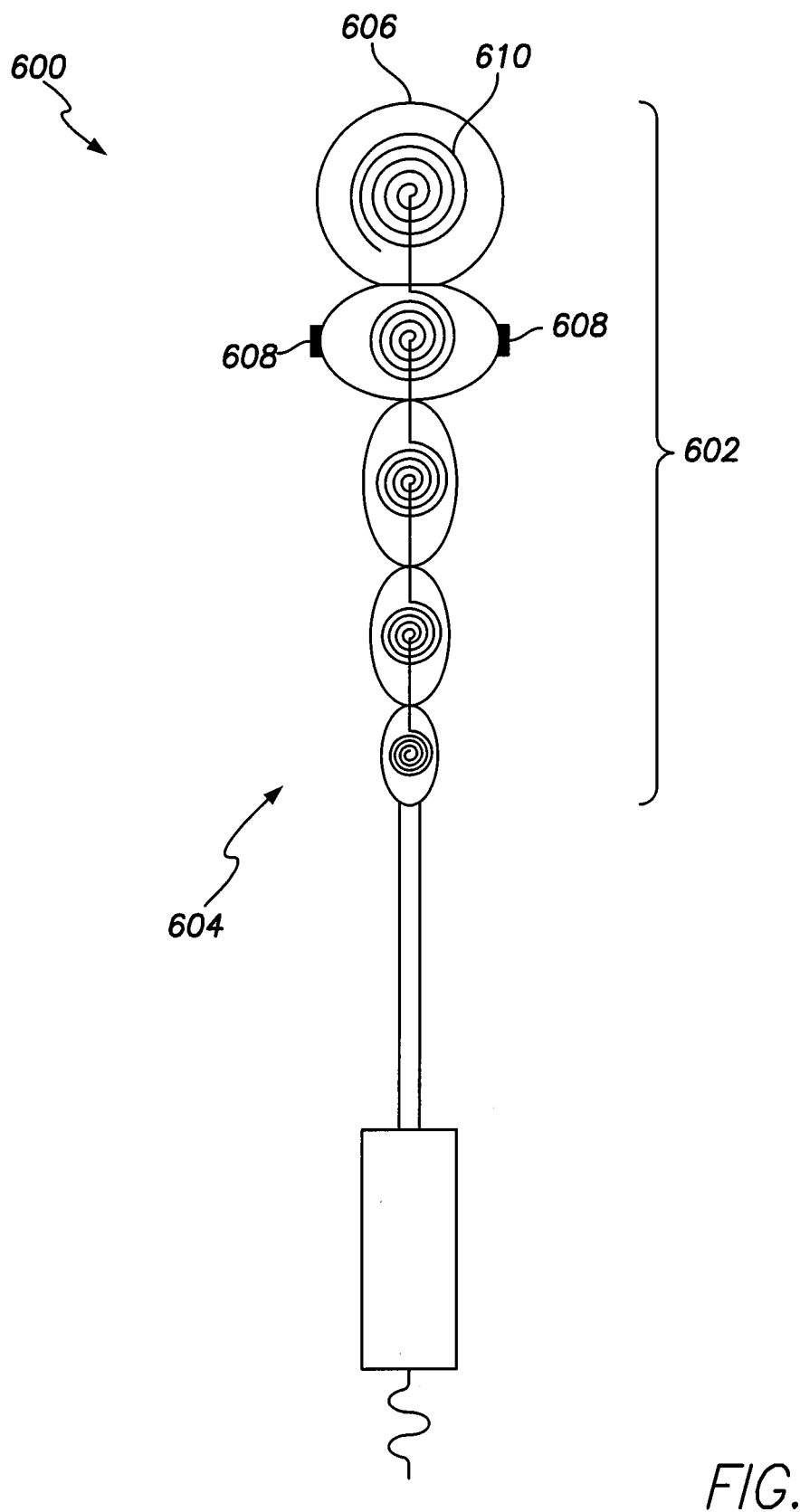
FIG. 6 illustrates another LIMD.

FIG. 6 illustrates an LIMD 600 according to another embodiment. The LIMD 600 is similar to the LIMD 100 illustrated in FIG. 4, except that this embodiment of the LIMD 600 includes an intra-cardiac extension 604 with a loop body 602 that is formed as a solid body without openings through loop segments 606. Additionally, electrodes 608 are secured to an outer portion of at least one of the loop segments 606. Because the loop segments 606 are contiguous, solid discs, as opposed to donut-shaped rings, a telemetry conductor 610 contained within each loop segment 606 may be contained within a greater area. As such, each loop segment 606 may include more windings.

Referring to FIGS. 4-6, the telemetry conductor 430, 610 may receive RF energy from an external programmer/handheld wireless control devices. The RF energy may represent wireless communications and/or power to recharge the battery 536. The handheld device may be a traditional programmer or may be a small portable device such as an iPOD-like device. The external device serves as a control unit that can upload and store data daily as well as program pacing/sensing parameters, pacing modes and device check-ups. The handheld device also provides transferring data to remote systems or patient home care systems. The handheld device may have a display screen for viewing signals and results. The programmer may be used to check battery life and to recharge the battery 536 by conveying battery power over the RF signal.

Referring to FIGS. 1-6, the LIMD 100, 600 may be contained within the introducer assembly 200, such as a flexible catheter. A physician or surgeon operates the introducer assembly at a proximal end (not shown). The proximal end may include controls that allow the introducer assembly to be bent, curved, canted, rotated, twisted, or the like, so as to be navigated through a patient's vasculature.

In order to implant the LIMD 100, 600 into the heart 12, the introducer assembly 200 containing the LIMD 100, 600 is introduced into a vein of a patient. During this time, a separate and distinct imaging system, such as a fluoroscopic imaging system, and/or a surgical navigation system may be used to assist in guiding the LIMD 100, 600 into the heart 12. For example, a surgeon may view a real-time fluoroscopic image of the patient's anatomy to see the compressed LIMD 100, 600 within the introducer assembly being maneuvered through patient anatomy.

The introducer assembly 200 is maneuvered through the vein and ultimately into the superior vena cava 22, for example, and into the right atrium 34. Optionally, the introducer assembly 200 may be maneuvered from a vein that connects to the inferior vena cava 23 and into the right atrium 34. Also alternatively, the introducer assembly 200 containing the LIMD 100, 600 may be introduced into other chambers of the heart through arteries, for example. In general, the LIMD 100, 600 may be introduced into a chamber of a heart through the introducer assembly 200.

Once in the heart 12, the housing 102 is implanted into tissue of the heart wall 12, such as proximate the apex 25 within the right ventricle 38. The securing helix 408 may securely fasten the housing 102 to the tissue of the heart wall. The protective tube 404 passes out of the right ventricle 38 and through the tricuspid valve 42. As the tubular catheter of the introducer assembly 200 slides out of engagement with the loop body 402, the compressed loop segments 421 eject from the introducer assembly 200 and assume their normally expand state within the heart 12. As shown, the loop segment 421a expands within the superior vena cava 22 such that the electrodes 420 contact interior wall portions of the superior vena cava 22. Additionally, other loop segments 421 may include electrodes that contact interior wall portions of the heart.

As shown in FIG. 1, the loop segments 421a and 421b may be configured to have diameters that may be larger than the inner diameter of the superior vena cava 22. In this manner, the loop segments 421a and 421b may be passively fixed to the superior vena cava 22, with the rest of the IMD 100 retained within the heart 12. In particular, the remaining loop segments 421 are within the right atrium 34, the protective sheath 404 passes through the tricuspid valve 42, and the body 406 housing 102 is secured to tissue of the right ventricle 38. The diameter of the loop segment 421b also ensures that the electrodes 420, which may be sensing and/or stimulus electrodes, abut against interior walls that define the superior vena cava 22.

Other loop segments 421 may be sized and shaped to make contact with wall portions that define the right atrium 34, for example, so that additional sensing and/or pacing electrodes abut against wall portions of the right atrium 34. Moreover, the LIMD 100 may be positioned within other chambers of the heart 12.

Thus, as shown, the LIMD 100, 600 is completely within the heart 12. No portion of the LIMD 100, 600 passes out of the heart. The loop body 402 is configured to be used in conjunction with a telemetry system to recharge the battery 536. Accordingly, a smaller battery may be used within the LIMD 100, 600 because it may be periodically re-charged. This is in contrast to a non-chargeable battery that typically needs to be large enough to provide sufficient power over a long period of time. Therefore, the form factor and overall size of the housing 102 may be compact.

Figure 7:
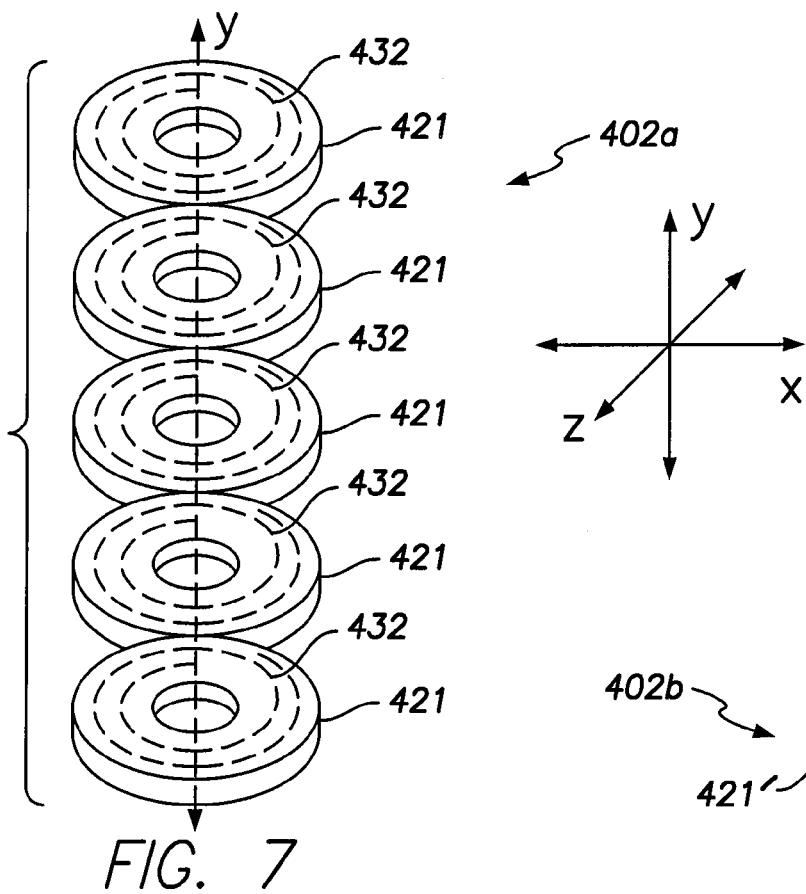
FIG. 7 illustrates a loop body of an LIMD.

FIG. 7 illustrates a loop body 402a, according to an embodiment. In this figure (and FIG. 8), the loop segments 421 are in the form of discs instead of rings (as shown in FIG. 4A) in order to more clearly illustrated the wound arrangement of coil groups 432. As shown in FIG. 7, the loop body 402a includes a plurality of loop segments 421. The loop segments 421 are generally aligned with one another about the longitudinal axis y. Each loop segment 421 may be coplanar with one another (as shown in FIG. 7). That is, if laid flat on a planar surface, all of the loop segment 421s would be contained within the same plane(s). In general, the loop segments 421 are oriented the same with respect to orthogonal axes x, y, and z. More or less loop segments 421 may be used. Further, one or more of the loop segments 421 may include sensing and/or stimulus electrodes, such as the electrodes 420 shown in FIG. 4A. Further, each loop segment 421 may be a donut-shaped segment having a central passage, such as shown and described with respect to FIGS. 4a and 4b, or a solid disc, such as shown and described with respect to FIG. 6.

Figure 8:
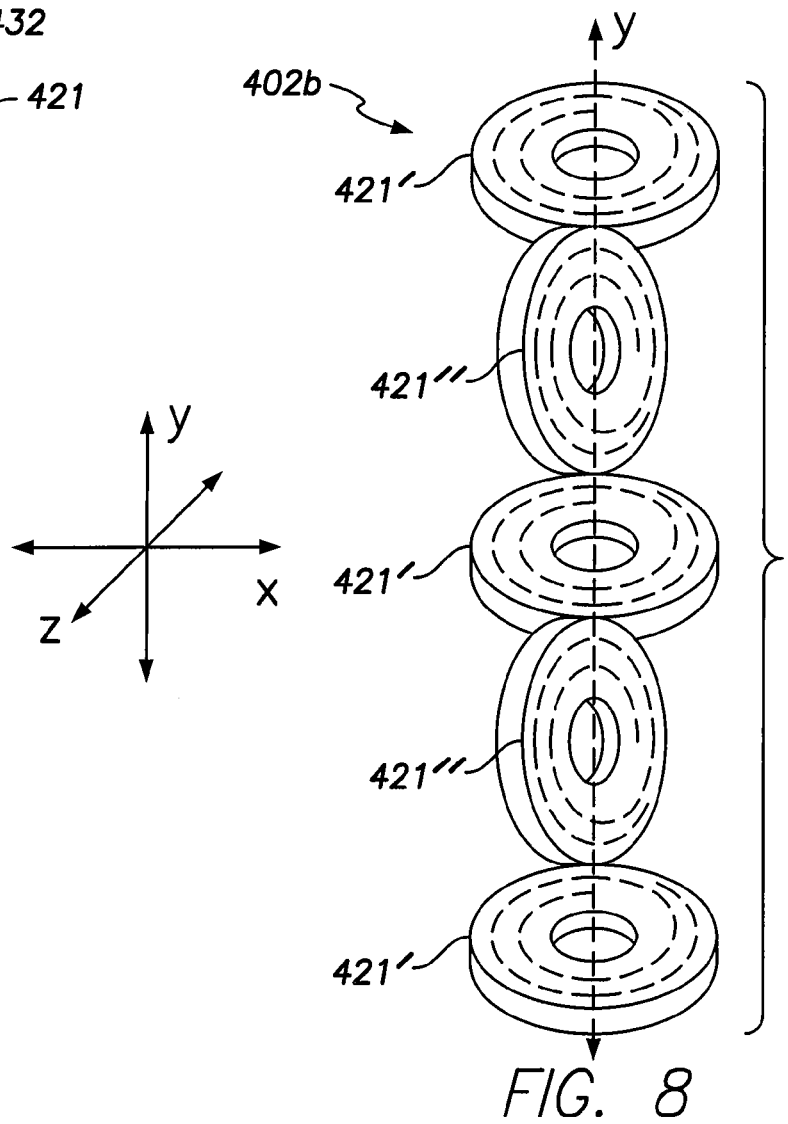
FIG. 8 illustrates another loop body of an LIMD.

FIG. 8 illustrates a loop body 402b, according to an embodiment. As shown in FIG. 8, the loop body 402b includes a plurality of first loop segments 421' connected to adjacent second loop segments 421". The first loop segments 421' are generally aligned and oriented in common with one another, while the second loop segments 421" are generally aligned and oriented in common with one another. However, each first loop segment 421' may be generally 90° out of plane with each second loop segment 421" with respect to the orthogonal axes x, y, and z. For example, while the first loop segments 421' are oriented along the x and y axes, the second loop segments 421" are oriented along the y and z axes. More or less first and second loop segments 421', 421" may be used. Further, one or more of the first or second loop segments 421', 421" may include sensing and/or stimulus electrodes. Further, each loop segment 421', 421" may be a donut-shaped segment having a central passage, such as shown and described with respect to FIGS. 4a and 4b, or a solid disc, such as shown and described with respect to FIG. 6. Optionally, the loop segments 421', 421" may be out of plane at other angles besides 90°. For example, the loop segments 421', 421" may be out of plane by 360°/number of loops. For example, if the loop body 402b includes three loop segments, each segment may be 120° out of plane with respect to a neighboring loop segment.

The loop segments may be oriented with respect to other planes. For example, one loop segment may be out plane with another loop segment, which may be out of plane with respect to another loop segment. The loop segments may be oriented with respect to different planes in relation to one another so that they may be oriented with respect to different magnetic fields (generated by RF energy) passing through the loop body 402b. A magnetic field induces a current in the conductive wire of the loop. Orienting the loop segments at varying angles allows the loop segments to provide recharging power to the battery and communicate with the telemetry circuit 450. Thus, if current from a magnetic field is not induced through a first loop segment due to its orientation with respect to the planes x, y, and z, current will be induced through a second and/or third loop segment that are oriented differently from the first loop segment.

A changing magnetic flux induces an electromotive force (emf) and a current in the coil groups 432 of the loop segments 421. A changing magnetic flux produces an electric field in the coil groups 432. Varying the orientations of the loop segments allows them to harness current induced by changing magnetic fields, and therefore pass that induced current to the rechargeable battery 536 of the housing 102.

Figure 9:
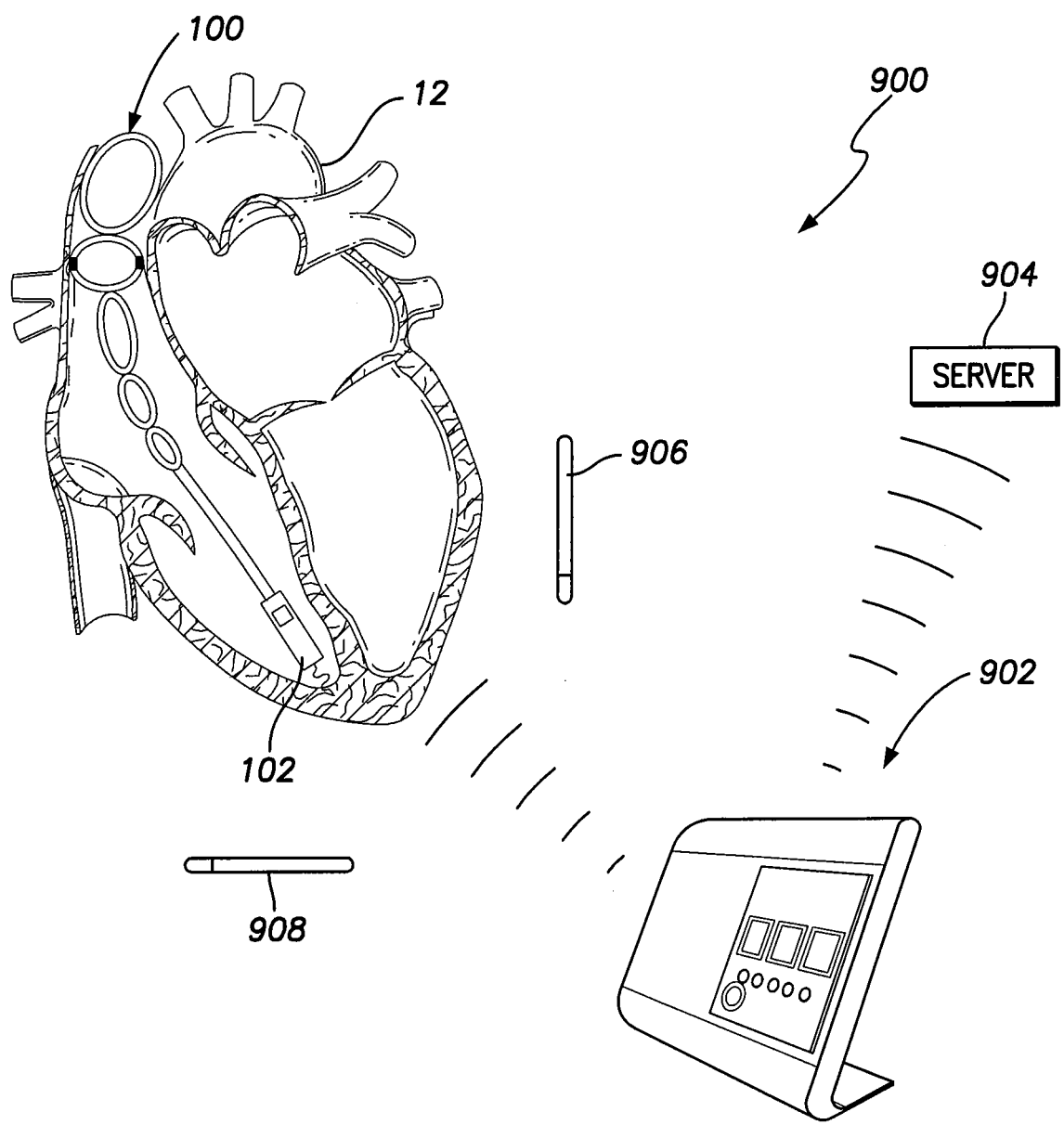
FIG. 9 is a simplified view of an LIMD and a patient care system (PCS).

FIG. 9 is a simplified view of a patient care network 900. In one configuration, the network includes the LIMD 100, a patient care system (PCS) 902, and a server 904. The PCS 902 corresponds to the external device 526 in FIG. 5. As discussed above, the IMD 100 is located entirely within the heart 12 of a patient. The remotely-located PCS 902 monitors and communicated with the LIMD 100 through RF telemetry. The PCS 902 may be located within a home, vehicle, office, and the like. When, the PCS 902 is located within the patient's home, it may be proximate the patient's bed. The PCS 902 functions as a base station that wirelessly communicates with the LIMD 100. The PCS 902 also communications with the remote server 904 within the patient care network 900, such as over a phone link, cellular link, Internet connection, local area network, wide area network and the like.

The PCS 902 performs various functions, such as operating as an intermediate relay device to collect and store patient physiologic data, LIMD operational status data and the like. The PCS 902 then transmits the physiologic data, LIMD operational status data and other data to the remote server 904 of the patient care network. Physicians and other personnel can monitor the patient and collect data over the patient care network. Also, the PCS 902 may receive updates, upgrades and other LIMD control-related information from the patient care network and relay the LIMD control-related information to the LIMD 100.

When the LIMD 100 is in the presence of a magnetic field, such as caused by RF energy when a wand 906, 908 is proximate the LIMD 100, current flow is induced in the coil groups 432 within the loop segments 421. The induced current passes to the rechargeable battery 536 of the body 406 of the housing 102. In this manner, the battery 536 is recharged.

Figure 10:
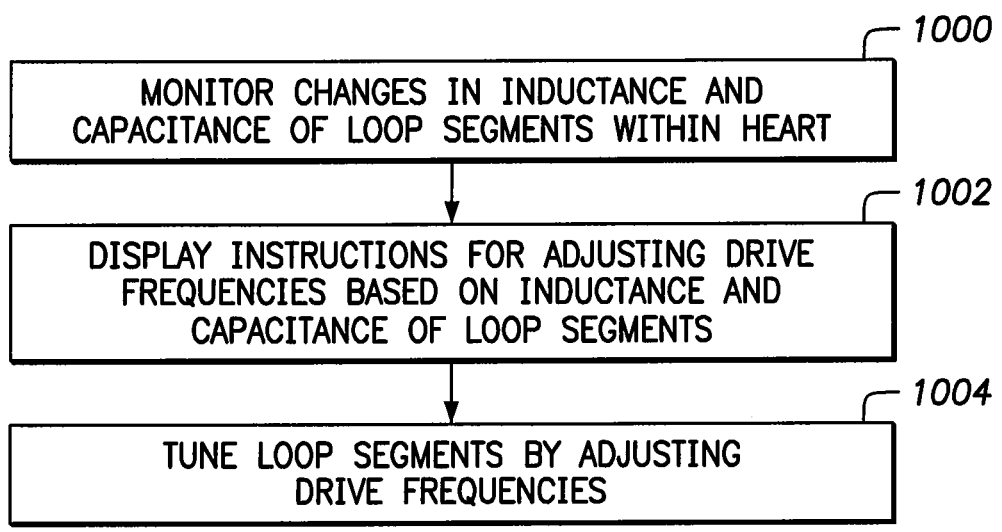
FIG. 10 illustrates a flow chart of calibrating an IMD.

FIG. 10 illustrates a flow chart of calibrating the LIMD 100, according to an embodiment of the present invention. Referring to FIGS. 1-5, 9, and 10, for example, the LIMD 100 may be calibrated after the LIMD 100 is implanted into the heart 12 of the patient. In general, the calibration process begins when an external device 526 (FIG. 5) (e.g. PCS 902 or programmer) instructs the LIMD 100 to enter a calibration mode. The external device 526 then begins to transmit a predetermined RF signal to the LIMD 100. The LIMD 100 may provide feedback to the external device 526 from the LIMD 100. The external device 526 may instruct a physician, technician or a patient how to optimize charging and communication properties of the LIMD 100 and external device 526.

Each patient exhibits a different anatomical shape and thus the loop segments 421 may experience different amounts/degrees of couple to the external wand of the external device 526 based on the patient. To compensate for these differences in individuals, the resonant frequencies of the coil groups 432 within the loop segments 421 may be tuned and adjusted by adjusting one or both of the capacitance and inductance within the RF antenna system created by the coil groups 432 and the electronics of the IMD 100. For example, the telemetry circuit 450 may have a variable inductor or capacitor therein that can be adjusted to change the resonant frequency of the loop segments 421.

As the loop segments 421 move within the heart 12 (due to patient movement, contractions of the heart, and the like), the shapes of the coil groups 432 change, thereby also potentially causing inductance and capacitance to change. The physician or patient may monitor these changes through the external device 526. Therefore, at 1000, a physician monitors changes in inductance and capacitance of the loop segments 421 within the heart 12.

At 1002, the display of the external device 526 may then display instructions for adjusting drive frequencies of the IMD 100 and/or positions of the wands 906, 908 in relation to the IMD 100. A change in drive frequency, such as 50 Hz±5 Hz, and/or the presence of the RF field generated by the wands 906, 908, may be used to compensate for the changing inductance and capacitance within the coil groups 432.

At 1004, the physician or technician may tune the loop segments 421 by adjusting the drive frequencies based on instructions shown on the display of the external device 526. The external device 526 may instruct the physician or patient how best to optimize the driving frequency of the LIMD 100 in order to optimize battery recharging, and communication between the LIMD 100 and the external device 526. Optionally, the physician may use the external device 526 to program the LIMD 100 with new values for resonant frequency parameters. Optionally, the LIMD 100 may automatically adjust its capacitance and/or inductance to achieve automated self tuning.

Figure 11:
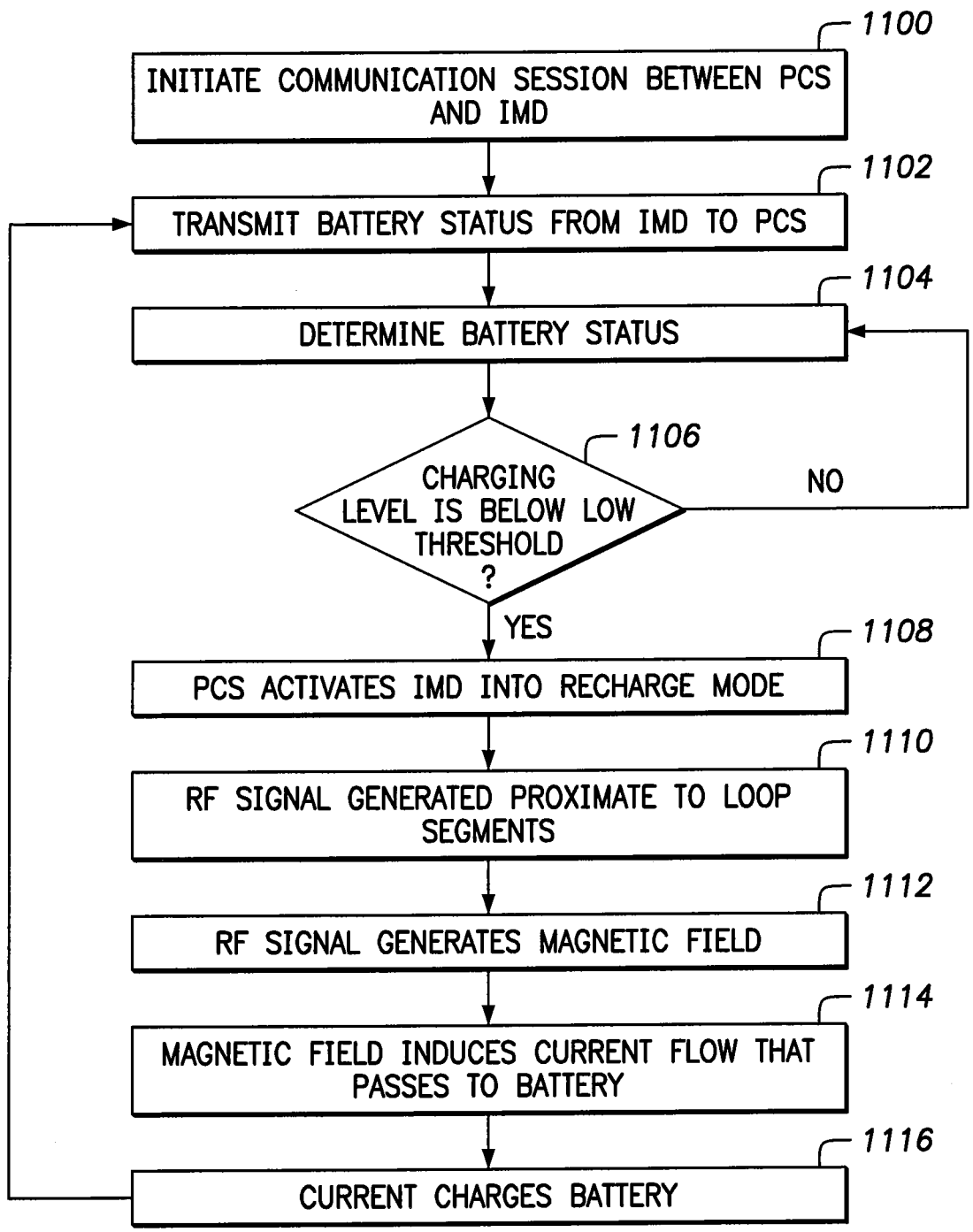
FIG. 11 illustrates a flow chart of a process of recharging an IMD.

FIG. 11 illustrates a flow chart of a process of recharging an LIMD, according to an embodiment. At 1100, a communication session is initiated between a patient care system (PCS) and the LIMD. Next, at 1102, the LIMD transmits battery status to the PCS. The PCS then determines the battery status at 1104. If, at 1106, the charging level of the battery within the LIMD is above a low battery threshold, the process returns to 1104. If, however, the charging level of the battery is at or below the low battery threshold, the PCS activates the LIMD into a recharge mode at 1108. In the recharge mode, an RF signal is generated proximate the loop segments of the LIMD at 1110. That is, the loop segments are in the presence of RF energy. The RF energy generates a magnetic field at 1112. The magnetic field induces current flow within the LIMD that passes from the loop segments to the rechargeable battery within the housing at 1114. The current then charges the battery at 1116. The process then returns to 1102.

Referring again to FIGS. 1-5, for example, as noted, an excitation RF signal induces current flow in the coil groups 432 within the loop segments 421. The current flows from the loop segments 421 to the body 406 of the housing 102 as an AC signal, thereby generating a voltage of between 1-10 V, for example, at the body 406 of the housing 102. If the voltage is too low to recharge the battery 536, the voltage may be stepped up to a suitable voltage, such as 3-6 V, for example. If the voltage is sufficient for charging, there is no need to step up the voltage. The AC current may then pass through a rectifier having diodes that rectify the signal to DC. The DC signal may then be filtered and passed to a voltage regulating circuit that monitors battery voltage, current, and temperature of the battery 536 to protect against over-charging or damaging the battery. For example, if the battery 536 is heating up too fast, the charging process may be slowed or halted altogether. The electronics describe above may be included in the telemetry circuit 450 of the housing 102.

Figure 12:
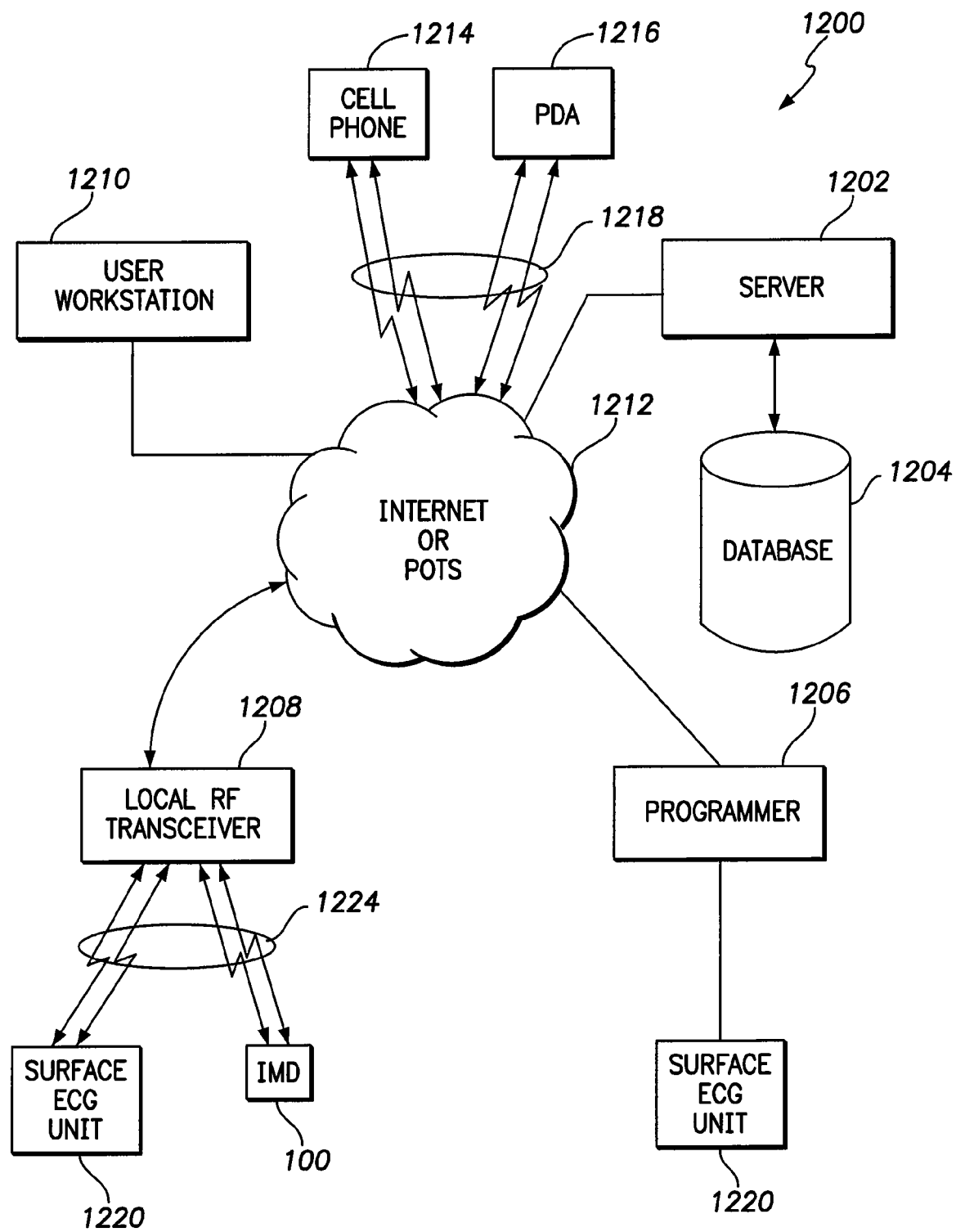
FIG. 12 illustrates a system that may be utilized in connection with an IMD, according to an embodiment.

FIG. 12 illustrates a system network 1200 that may be utilized in connection with the LIMD 100 (FIG. 4) or 600 (FIG. 6), according to an embodiment. The system network 1200 may include a server 1202 connected to a database 1204, a programmer 1206, a local RF transceiver 1208 and a user workstation 1210 electrically connected to a communication system 1212. The communication system 1212 may be the internet, a voice over IP (VoIP) gateway, a local plain old telephone service (POTS) such as a public switched telephone network (PSTN), a cellular phone based network, and the like. Alternatively, the communication system 1212 may be a local area network (LAN), a campus area network (CAN), a metropolitan area network (MAN), or a wide area network (WAM). The communication system 1212 serves to provide a network that facilitates the transfer/receipt of information.

The system 1200 includes the LIMD 100, for example, implemented in accordance with embodiments discussed. The LIMD 100 may be located within a heart of a patient, as discussed above.

The server 1202 is a computer system that provides services to other computing systems over a computer network. The server 1202 interfaces with the communication system 1212 to transfer information between the programmer 1206, the local RF transceiver 1208, the user workstation 1210 as well as a cell phone 1214, and a personal data assistant (PDA) 1216 to the database 1204 for storage/retrieval of records of information. On the other hand, the server 1202 may upload raw cardiac signals from a surface ECG unit 1220 or the LIMD 100 via the local RF transceiver 1208 or the programmer 1206.

The database 1204 stores information such as the measurements for the electrical cardiac signals, the electrophysiologic response parameters, and the like, for a single or multiple patients. The information is downloaded into the database 1204 via the server 1202 or, alternatively, the information is uploaded to the server from the database 1204. The programmer 1206 may reside in a patient's home, a hospital, or a physician's office. Programmer 1206 interfaces with the surface ECG unit 1220 and the LIMD 100. The programmer 1206 may wirelessly communicate with the LIMD 100 and utilize protocols, such as Bluetooth, GSM, infrared wireless LANs, HIPERLAN, 3G, satellite, as well as circuit and packet data protocols, and the like. The programmer 1206 is able to acquire cardiac signals from the surface of a person (e.g., ECGs), intra-cardiac electrogram (e.g., IEGM) signals from the LIMD 100, and/or values of cardiogenic impedance parameters and electrophysiologic response parameters from the LIMD 100. The programmer 1206 interfaces with the communication system 1212, either via the internet or via POTS, to upload the information acquired from the surface ECG unit 1220 or the LIMD 100 to the server 1202.

The local RF transceiver 1208 interfaces with the communication system 1212, via a communication link 1224, to upload data acquired from the surface ECG unit 1220 and/or from LIMD 100 to the server 1202. In one embodiment, the surface ECG unit 1220 and the LIMD 100 have a bi-directional connection with the local RF transceiver via a wireless connection. The local RF transceiver 1208 is able to acquire cardiac signals from the LIMD 100. On the other hand, the local RF transceiver 1208 may download stored data, parameters, cardiac data, and the like, from the database 1204 to the LIMD 100.

The user workstation 1210 may interface with the communication system 1212 via the internet or POTS to download values of the cardiogenic impedance parameters and electrophysiologic response parameters via the server 1202 from the database 1204. Alternatively, the user workstation 1210 may download raw data from the surface ECG unit 1220 or LIMD 100 via either the programmer 1206 or the local RF transceiver 1208. The user workstation 1210 may download the information and notifications to the cell phone 1214, the PDA 1216, the local RF transceiver 1208, the programmer 1206, or to the server 1202 to be stored on the database 1204. For example, the user workstation 1210 may communicate an identified potential cause of pulmonary edema to the cell phone 1214 of a patient or physician.

As explained above, embodiments provide an implantable medical device (IMD) that is compact and configured to be retained within chambers of a heart. Moreover, because the battery of the IMD is rechargeable, a smaller, less bulky battery may be used, as compared to known systems. Therefore, a housing of the IMD may be smaller and occupy a relatively small volume within the heart.

Embodiments herein utilize an intra-cardiac extension having a distal extension portion that is pre-formed into planar disc-shaped segments. A proximal end of the IC extension is coupled to a housing. The proximal end of the IC extension is configured to be located in a local chamber of the heart, while the distal extension portion is configured to extend into an adjacent chamber of the heart. For example, the housing and proximal end of the IC extension may be located in the right ventricle or left ventricle, while the distal extension portion of the IC extension extends through the tricuspid or mitral valve, respectively, into the corresponding one of the right atrium or left atrium.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A leadless intra-cardiac medical device (LIMD) configured to be implanted entirely within a heart of a patient, the LIMD comprising:
   an intra-cardiac extension comprising a loop body, the loop body comprising at least one loop segment, the loop segment comprising at least one coil group that is configured to one or both of receive and transmit radio frequency (RF) energy, wherein the loop body is configured to extend into a first chamber of the heart; and
   a housing in electrical communication within the loop body, the housing comprising a transceiver, wherein the housing is configured to be securely attached to an interior wall portion of a second chamber of the heart, wherein the transceiver is configured to communicate with an external device through the RF energy, wherein the at least one loop segment is distally located from the housing and further comprises a contiguous, solid disc and at least one electrode, wherein the electrode is secured to an outer portion of the loop segment.

2. The device of claim 1, wherein the housing further comprises an energy source configured to be recharged through current induced within the at least one coil group, and wherein the current is induced by a magnetic field caused by the RF energy.

3. The device of claim 1, wherein the at least one loop segment is configured to contact a portion of an internal wall of the heart, and wherein the housing further comprises electronics configured to provide one or both of sensing or stimulus through the at least one electrode.

4. The device of claim 1, wherein the at least one loop segment includes a plurality of interconnected loop segments.

5. The device of claim 4, wherein each of the plurality of interconnected loop segments are commonly aligned and oriented with respect to one another.

6. The device of claim 4, wherein the plurality of interconnected loop segments includes a first group of loop segments and a second group of loop segments, wherein the first group of loop segments is oriented with respect to first and second orthogonal axes and the second group of loop segments is oriented with respect to first and third orthogonal axes.

7. The device of claim 4, wherein a first of the plurality of interconnected loop segments is aligned in a first orientation and a second of the plurality of interconnected loop segments is aligned in a second orientation, and wherein the first orientation differs from the second orientation so that the first and second of the plurality of interconnected loop segments are out of plane with one another.

8. The device of claim 1, wherein the at least one loop segment comprises a perimeter that flares in a direction generally toward and away from a lateral axis with respect to a longitudinal axis of the loop body.

9. The device of claim 1, further comprising a protective tube between the loop body and the housing.

10. A leadless intra-cardiac medical device (LIMD) configured to be implanted entirely within a heart of a patient, the device comprising:
    a housing configured to be securely attached to an interior wall portion of a first chamber of the heart, the housing having a proximal end and a distal end, and the housing hermetically enclosing a telemetry circuit, the telemetry circuit comprising a transceiver, wherein the transceiver is configured to communicate with an external device through radio frequency (RF) energy; and
    an intracardiac (IC) extension extending from the distal end of the housing, the IC extension having a proximal end directly connected to the distal end of the housing, the IC extension having a distal end comprising a loop body configured to extend into a second chamber of the heart, the loop body comprising at least one loop segment, the loop segment comprising at least one coil group, the coil group configured to one or both of receive and transmit the RF energy, wherein the loop segment has a resonant frequency, and wherein the telemetry circuit is configured to adjust the resonant frequency of the loop segment.

11. The leadless intra-cardiac medical device of claim 10, wherein the housing further comprising a battery, and wherein the coil group of the loop segment is configured to induce current flow and pass the current flow to the battery when the LIMD is in the presence of a magnetic field.

12. A leadless intra-cardiac medical device (LIMD) configured to be implanted entirely within a heart of a patient, the LIMD comprising:
    an intra-cardiac extension comprising a loop body, the loop body comprising at least one loop segment, the loop segment comprising at least one coil group that is configured to one or both of receive and transmit radio frequency (RF) energy, wherein the loop body is configured to extend into a first chamber of the heart, wherein the at least one loop segment includes a plurality of interconnected loop segments, wherein the plurality of interconnected loop segments includes a first group of loop segments and a second group of loop segments, wherein the first group of loop segments is oriented with respect to first and second orthogonal axes and the second group of loop segments is oriented with respect to first and third orthogonal axes; and
    a housing in electrical communication within the loop body, the housing comprising a transceiver, wherein the housing is configured to be securely attached to an interior wall portion of a second chamber of the heart, wherein the transceiver is configured to communicate with an external device through the RF energy.

13. The device of claim 12, wherein the at least one loop segment comprises a perimeter shaped as a disc, oval, circle, tube, rectangle, or triangle.

* * * * *